(12) United States Patent
Owsley et al.

(10) Patent No.: US 8,419,651 B2
(45) Date of Patent: Apr. 16, 2013

(54) SPECTRUM ANALYSIS OF CORONARY ARTERY TURBULENT BLOOD FLOW

(75) Inventors: Norman Lee Owsley, Gales Ferry, CT (US); Roger Paul Norris, Mystic, CT (US); Ralph Walter Zaorski, Davenport, FL (US)

(73) Assignee: Phonoflow Medical, LLC, Gales Ferry, CT (US)

( * ) Notice: Subject to any disclaimer, the term of this patent is extended or adjusted under 35 U.S.C. 154(b) by 1255 days.

(21) Appl. No.: 12/228,058

(22) Filed: Aug. 9, 2008

(65) Prior Publication Data

US 2010/0036254 A1    Feb. 11, 2010

(51) Int. Cl.
*A61B 5/02*         (2006.01)
*A61B 8/06*         (2006.01)

(52) U.S. Cl.
USPC ............................ 600/528; 600/454; 600/437

(58) Field of Classification Search .................. 600/528, 600/413, 493
See application file for complete search history.

(56) References Cited

U.S. PATENT DOCUMENTS

| | | | | | |
|---|---|---|---|---|---|
| 4,446,873 | A | * | 5/1984 | Groch et al. | 600/528 |
| 5,036,857 | A | * | 8/1991 | Semmlow et al. | 600/528 |
| 6,116,080 | A | * | 9/2000 | Logue et al. | 73/24.05 |
| 6,771,999 | B2 | * | 8/2004 | Salla et al. | 600/413 |
| 2006/0155204 | A1 | * | 7/2006 | Wariar et al. | 600/528 |

OTHER PUBLICATIONS

International Search Report for Application PCT/US2009/004511, Aug. 5, 2009 (3 pages).
Written Opinion for Application PCT/US2009/004511, Aug. 5, 2009 (4 pages).

* cited by examiner

*Primary Examiner* — Carl H. Layno
*Assistant Examiner* — Jon-Eric C. Morales
(74) *Attorney, Agent, or Firm* — Peloquin, PLLC; Mark S. Peloquin, Esq.

(57) ABSTRACT

A method includes acquiring vibrational cardiac data from an array of N transducers wherein the transducers are coupled to a human. A master replica is selected from a segment of the vibrational cardiac data. The master replica is correlated with the segment to obtain a plurality of local maxima. Vibrational cardiac data that were emitted during a diastolic interval are extracted from each heart cycle with the aid of the plurality of local maxima. A two-dimensional space-time frequency power spectrum is processed for Equivalent Rectangular Bandwidth, which provides estimates of the energy produced by turbulent blood flow through a coronary stenosis.

52 Claims, 15 Drawing Sheets

SPECTRUM ANALYSIS OF CORONARY ARTERY TURBULENT BLOOD FLOW

BACKGROUND OF THE INVENTION

1. Field of Invention

The invention relates generally to detecting and processing vibrational cardiac data, and more specifically to apparatuses and methods used to detect vibrational cardiac data related to coronary artery disease.

2. Art Background

Coronary artery disease is a primary precursor of heart attacks, which is a leading cause of death in the United States. Coronary artery disease is characterized by a deposition of plaque within the coronary arteries, resulting in a condition referred to as stenosis, in which case blood flow is restricted and the oxygen supply to the heart muscle is decreased. Such a deposition of plaque is also referred to as an occlusion. Coronary artery disease can result in heart attack and subsequent physical injury and possible death. This can present a problem.

It is known that the blood flow can become turbulent as the blood passes through an area of stenosis. Turbulent blood flow provides a source of vibrational excitation within the body. The vibrational excitation causes energy to propagate through the body and provides a field that can be measured at the surface of the body. Normal body functions such as breathing and the opening and closing of the heart's valves provide high levels of background noise relative the magnitude of the vibrational energy resulting from excitation at areas of stenosis. Such high levels of background noise can frustrate detection. This can present a problem.

The body is made up of structures that have very different physical properties which are distributed as a function of space throughout the body cavity. Some of these structures are lungs, ribs, organs, blood, arteries, fat, etc. These structures present a non-homogeneous media to the propagation of vibrational energy. Such a non-homogenous media can make it difficult to characterize the media sufficiently to form focused listening beams while processing the vibrational energy emitted from the areas of stenosis during a parametric analysis that assumes a known vibrational wave speed. This can present a problem.

Currently, coronary artery disease is treated post symptomatically with an invasive procedure called an angiogram. The angiogram is costly, invasive, and places the patient at risk of injury due to complications that can arise during the procedure. All of this can present problems.

BRIEF DESCRIPTION OF THE DRAWINGS

The invention may best be understood by referring to the following description and accompanying drawings that are used to illustrate embodiments of the invention. The invention is illustrated by way of example in the embodiments and is not limited in the figures of the accompanying drawings, in which like references indicate similar elements.

DETAILED DESCRIPTION

In the following detailed description of embodiments of the invention, reference is made to the accompanying drawings in which like references indicate similar elements, and in which is shown by way of illustration, specific embodiments in which the invention may be practiced. These embodiments are described in sufficient detail to enable those of skill in the art to practice the invention. In other instances, well-known circuits, structures, and techniques have not been shown in detail in order not to obscure the understanding of this description. The following detailed description is, therefore, not to be taken in a limiting sense, and the scope of the invention is defined only by the appended claims.

Apparatuses and methods are described for detecting and processing vibrational cardiac data in a human. In one or more embodiments, the vibrational cardiac data arises from stenosis in a coronary artery. In one embodiment, vibrational cardiac data is measured and processed from a phantom with and without stenosis.

Figure 1A:
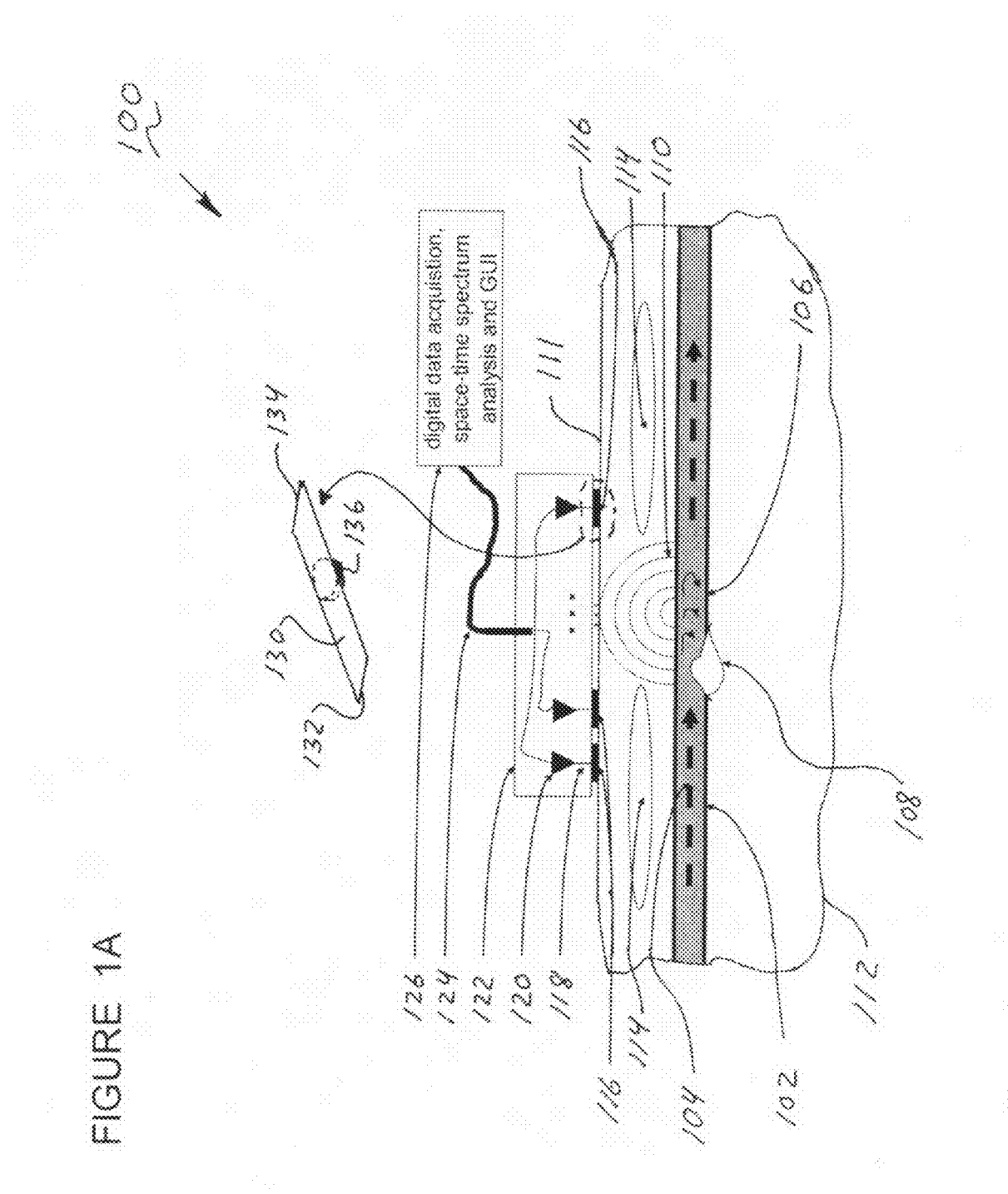
FIG. 1A illustrates an apparatus, according to one embodiment of the invention.

FIG. 1A illustrates an apparatus generally at 100, according to one embodiment of the invention. With reference to FIG. 1A, a cross-section 101 of a human body contains coronary artery 102 having a flow of blood 104 passing therethrough. The flow of blood 104 can interact with a coronary artery lesion 108 and cause an excitation of the artery wall by known physical means, which include transition to turbulent flow and the corresponding application of forces normal to the surface of the coronary artery. Such excitation of the coronary artery wall results in vibrational energy 110 propagating to the surface of the human 111.

In this description of embodiments, the term "sensor" is synonymous with the terms "channel" or "sensor channel," whereby a separate measurement is contemplated. Additionally, the term "sensor" is synonymous with the terms "transducer" or "sensing transducer." Thus, a first sensor's output (a first channel) and a second sensor's output (a second channel) are each available for analysis and each represents a separate measurement of a field quantity of interest, such as the vibration field in a human's body. As will be noted by those of skill in the art, in some instances, it might be advantageous to electrically combine together, in series or parallel, several sensors into a single channel. Such combinations can be made within the scope of the descriptions provided herein. However to simplify the discussion, "sensor" will be understood to be synonymous with the terms "sensor channel," "channel," "transducer," or "sensing transducer."

An array of sensors 116 measures the vibration of the surface 111 and collects vibrational cardiac data thereby. The array of sensors 116 is made up of a general number of N sensors (sensing transducers or transducers). In one embodiment, the number N equals 14 and the spacing between adjacent transducers is one-quarter inch (0.25"). Those of skill in the art will recognize that the array of N sensors 116 can be configured with; a different number of sensors, a different sensor width, and/or sensor spacing. The example given herein is provided merely for illustration and does not limit embodiments of the invention.

The cross section 101 of the human presents a non-homogeneous media through which the vibrational energy 110 propagates and contains various structures such as ribs, lungs, organs interfaces, muscles, fat, and skin tissue indicated generally by 114. The vibrational energy propagates through the non-homogeneous media and is measured on the surface 111 by the array of N sensors 116. In one embodiment, it can be desirable to place the array of sensors 116 over a person's heart and above a space between adjacent ribs to facilitate detection of the vibrational energy.

In one embodiment, each sensor of the array of sensors 116 is made from a strip of polyvinylidene fluoride (PVDF) film. In one example, each strip of PVDF film measures 0.75 inches long, between attachments to a chassis 122, and 0.1875 inches wide. Each strip of PVDF film is stretched into a flat plane and is anchored at each end by the chassis 122. At the midpoint of each strip of PVDF film, a pad is placed to provide an area of contact between the skin surface 111 and the strip of PVDF film. An example of one such sensor from the array of sensors 116 is illustrated by a strip of PVDF film 130, having a first end 132 and a second end 134 (which are attached to the chassis 122 ) and a pad 136 that makes contact with the skin surface 111. In one embodiment, the diameter of the pads is 0.1875 inches and the thickness of the pads is 0.0625 inches. The sensitivity of the PVDF film along its major axis is 22176 V/unit strain for a PVDF film thickness of 0.028 millimeters. The PVDF film generates a voltage in response to strain imparted from the motion of the skin surface 111. In one embodiment, the chassis 122 is made out of metal such as aluminum, in other embodiments the chassis 122 is made out of plastic or another material sufficient to provide the necessary anchor points for the strips of PVDF film.

Each sensing transducer is in electrical contact with at least one preamplifier 120 using connection 118. It is advantageous to place a preamplifier proximate to its sensing transducer in order to minimize the addition of electronic noise. Additional amplification stages can be used and in one embodiment the outputs from the preamplifiers 120 are passed to a bank of amplifiers (not shown), such as those available from Ithaco Corporation Model 451. In one embodiment, the outputs of the sensing transducers (array 116) are carried in a cable bundle 124 and are processed in a data acquisition system 126 that can contain a graphical user interface (GUI).

Those of skill in the art will appreciate that adjustments to the array geometry can be made, i.e., sensor dimensions and sensor spacing. Vibrational energy 110 includes shear wave energy propagation with shear wavelengths on the order of several tens of millimeters, e.g. approximately 40 millimeters at 200 cycles per second and approximately 20 millimeters at 500 cycles per second.

Figure 1B:
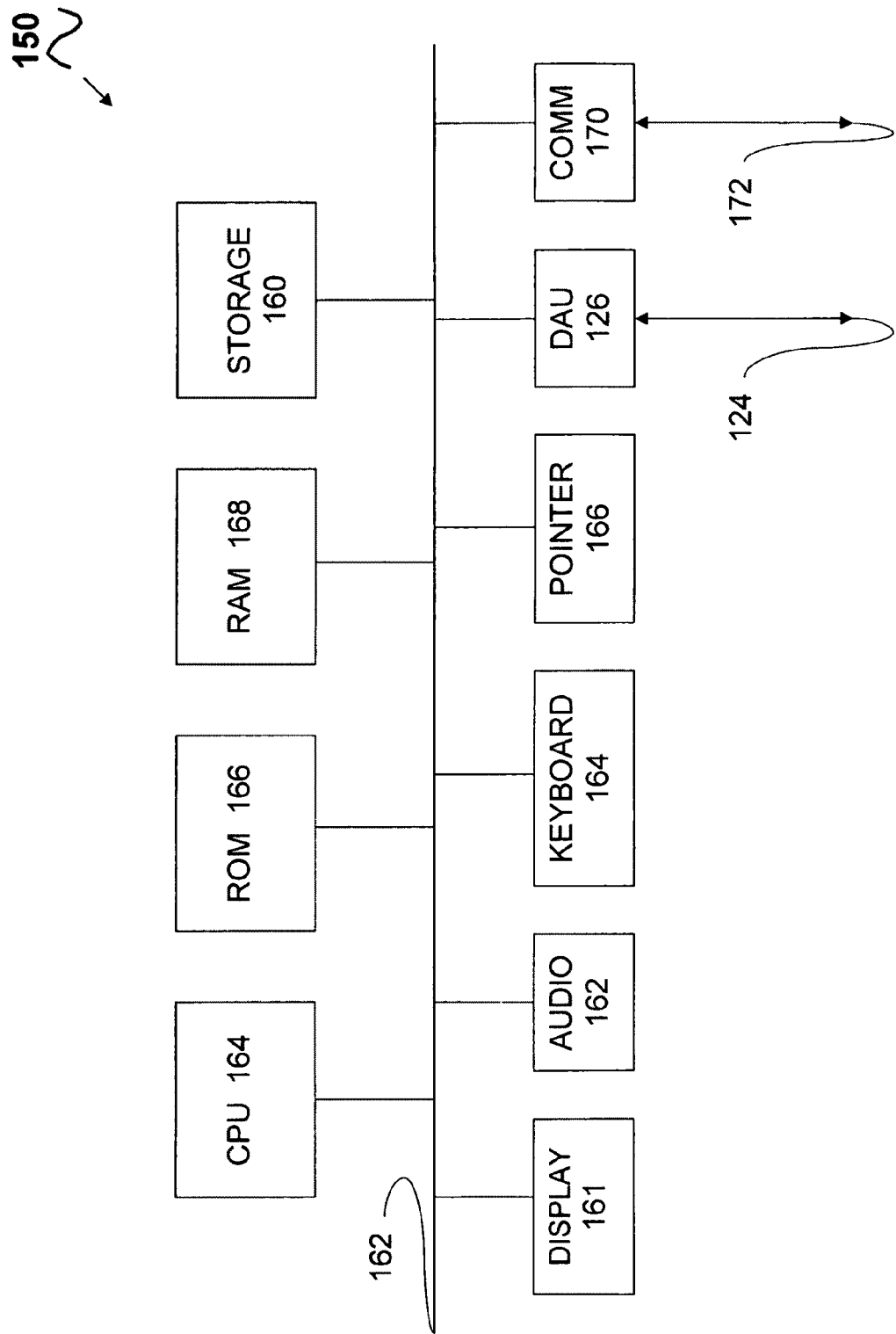
FIG. 1B illustrates a block diagram of a computer system (data acquisition system) in which embodiments of the invention may be used.

FIG. 1B illustrates, generally at 150, a block diagram of a computer system (data acquisition system) in which embodiments of the invention may be used. The block diagram is a high-level conceptual representation and may be implemented in a variety of ways and by various architectures. With reference to FIG. 1B, bus system 162 interconnects a Central Processing Unit (CPU) 164, Read Only Memory (ROM) 166, Random Access Memory (RAM) 168, storage 160, display 161, audio 162, keyboard 164, pointer 166, data acquisition unit (DAU) 126, and communications 170. The bus system 162 may be for example, one or more of such buses as a system bus, Peripheral Component Interconnect (PCI), Advanced Graphics Port (AGP), Small Computer System Interface (SCSI), Institute of Electrical and Electronics Engineers (IEEE) standard number 1394 (FireWire), Universal Serial Bus (USB), or a dedicated bus designed for a custom application, etc. The CPU 164 may be a single, multiple, or even a distributed computing resource. Storage 160 may be Compact Disc (CD), Digital Versatile Disk (DVD), hard disks (HD), optical disks, tape, flash, memory sticks, video recorders, etc. The computer system 150 can be used to receive vibrational cardiac data via 124 from the array 116 of vibration sensors (FIG. 1A). Note that depending upon the actual implementation of a computer system, the computer system may include some, all, more, or a rearrangement of components in the block diagram.

Thus, in various embodiments, vibrational cardiac data is received at 124 for processing by the computer system 150. Such data can be transmitted via communications interface 170 for further processing and diagnosis in a remote location, as illustrated in FIG. 1B at 172. Connection with a network, such as an intranet or the Internet is obtained via 172, as is recognized by those of skill in the art, which enables the data processing device 150 to communicate with other data processing devices in remote locations.

For example, embodiments of the invention can be implemented on a computer system 150 configured as a desktop computer or work station, on for example a WINDOWS® compatible computer running operating systems such as WINDOWS® XP Home or WINDOWS® XP Professional, Linux, etc. as well as computers from APPLE COMPUTER, Inc. running operating systems such as OS X, etc. Alternatively, or in conjunction with such an implementation, embodiments of the invention can be configured within devices such as speakers, earphones, video monitors, etc. configured for use with a Bluetooth communication channel.

Figure 2:
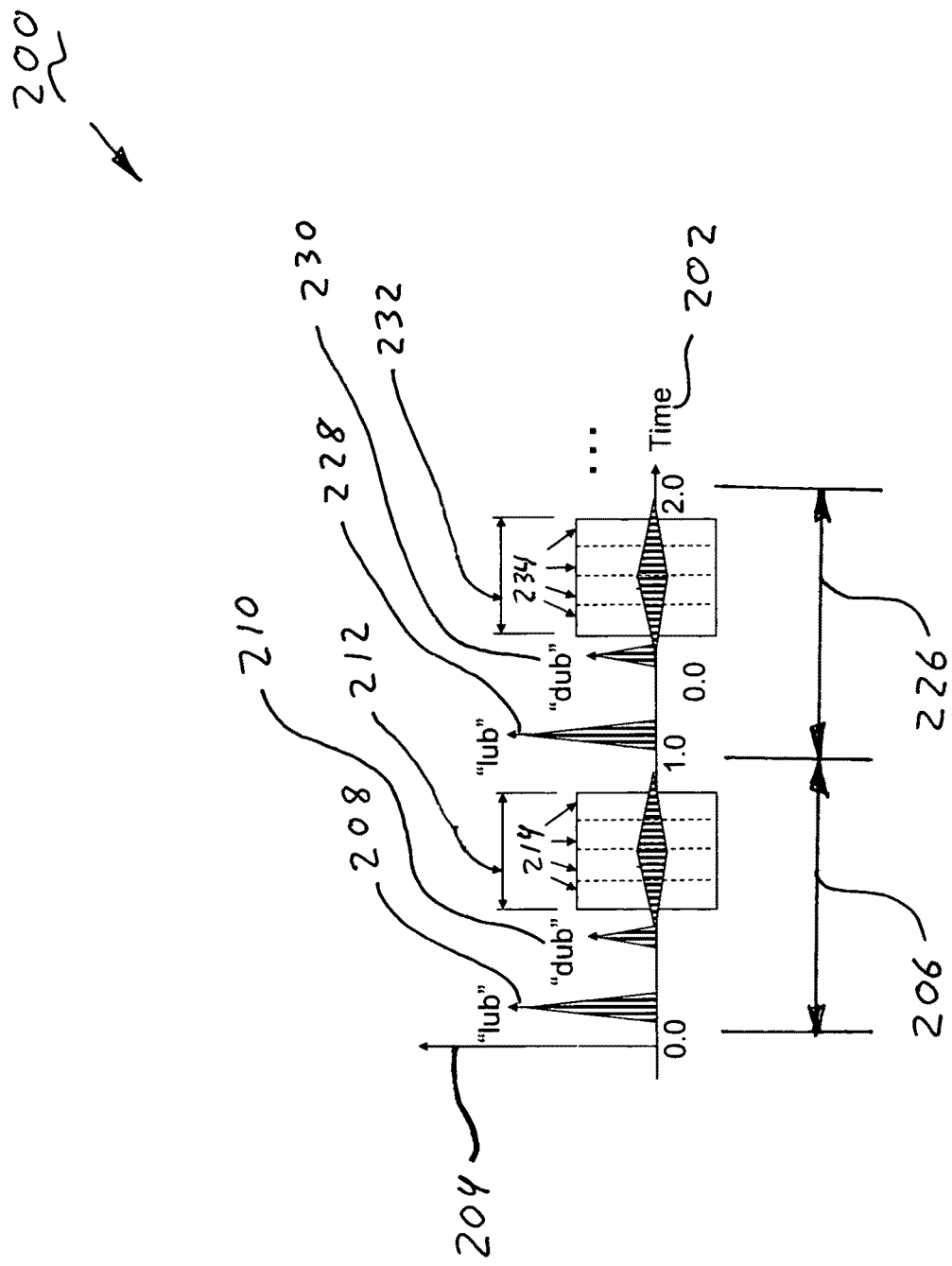
FIG. 2 illustrates a plot, representational of vibrational cardiac data as a function of time for two heart cycles, according to one embodiment of the invention.

FIG. 2 illustrates, generally at 200, a plot of vibrational cardiac data as a function of time for two heart cycles, according to one embodiment of the invention. With reference to FIG. 2, a representative output from one of the vibration sensors, from array 116 (FIG. 1A) is illustrated, where a magnitude of the sensor's output is plotted on a vertical axis 204 as a function of time 202. A first heart cycle 206 contains a first peak 208 corresponding to the closure of the mitral and tricuspid valves. This first peak is described in the literature as a "lub" sound when heard through a stethoscope. The first heart cycle 206 contains a second peak at 210, which corresponds to the closure of the two semi-lunar, aortic and pulmonary valves at the beginning of diastolic period 212. This second peak is described in the literature as a "dub" sound when heard through a stethoscope. The diastolic period 212 follows the second peak 210.

The heart continues to beat, and a second heart cycle 226 is produced thereby with the same major features found in the first heart cycle; a first peak at 228, followed by a second peak at 230, and a diastolic interval (DI) 232. Successive heart cycles (not shown) will continue to occur as the heart continues to beat. During the diastolic intervals, 212, 232, etc., blood flow is at a maximum in the coronary arteries and unwanted coronary events, such as the first peaks 208, 228 and the second peaks 210, 230 are separated in time and their effect on the diastolic interval is at a minimum.

In one embodiment, it is desirable to process vibrational cardiac data accumulated over approximately one hundred and twenty (120) heart cycles in order to provide a sufficiently long averaging time record length for an array of 14 channels. In practice, with human test subjects, it has been observed that the human test subjects can comfortably breath-hold for approximately twenty (20) heart cycles. In this case, a human test subject will alternate between breath-hold and normal breathing, for breath recovery, while the heart waveform is measured. In one embodiment, a nominal duration of the entire heart waveform is from one hundred and twenty (120) to one hundred and eighty (180) seconds and is made up of six (6) twenty (20) to thirty (30) second segments. In another embodiment, a number of heart cycles is approximately equal to ten (10) to fifteen (15) times the number of sensor channels in array N. Such a number of heart cycles is needed to adequately resolve the numerically higher eigenvalues as described below in sections of the following discussion. A shorter duration heart waveform (fewer heart cycles) can be collected if the eigenvalue range is limited accordingly. Those of skill in the art will appreciate that the entire heart waveform can vary in length and that the examples provided herein are given for illustration only and do not limit embodiments of the invention.

The number of heart cycles over which a human test subject can comfortably breath-hold will vary between human test subjects and will depend on many factors such as age, physical condition, etc. When vibrational cardiac data is collected during breath-hold, the effects of breathing on the measured vibrational cardiac data are minimized. The number of segments can be adjusted to suite the particular test conditions, given the length of time that the human test subject can breath-hold for and the number of sensor channels in the array N. In one embodiment, a human starts and stops the acquisition of the vibrational cardiac data to coincide with acquisition during breath-hold periods.

The N sensor array, described in FIG. 1A, is used to measure and process vibrational cardiac energy, which is measured at the surface 111 during the diastolic intervals. In one embodiment, such measurement and processing of the vibrational cardiac energy is used to determine whether a plaque deposit(s) (coronary artery lesion(s)) 108 exists in the human due to coronary artery disease. In other embodiments, such processing can be used to detect vibrational energy generated within the human in general and not necessarily caused by coronary artery disease.

Figure 3:
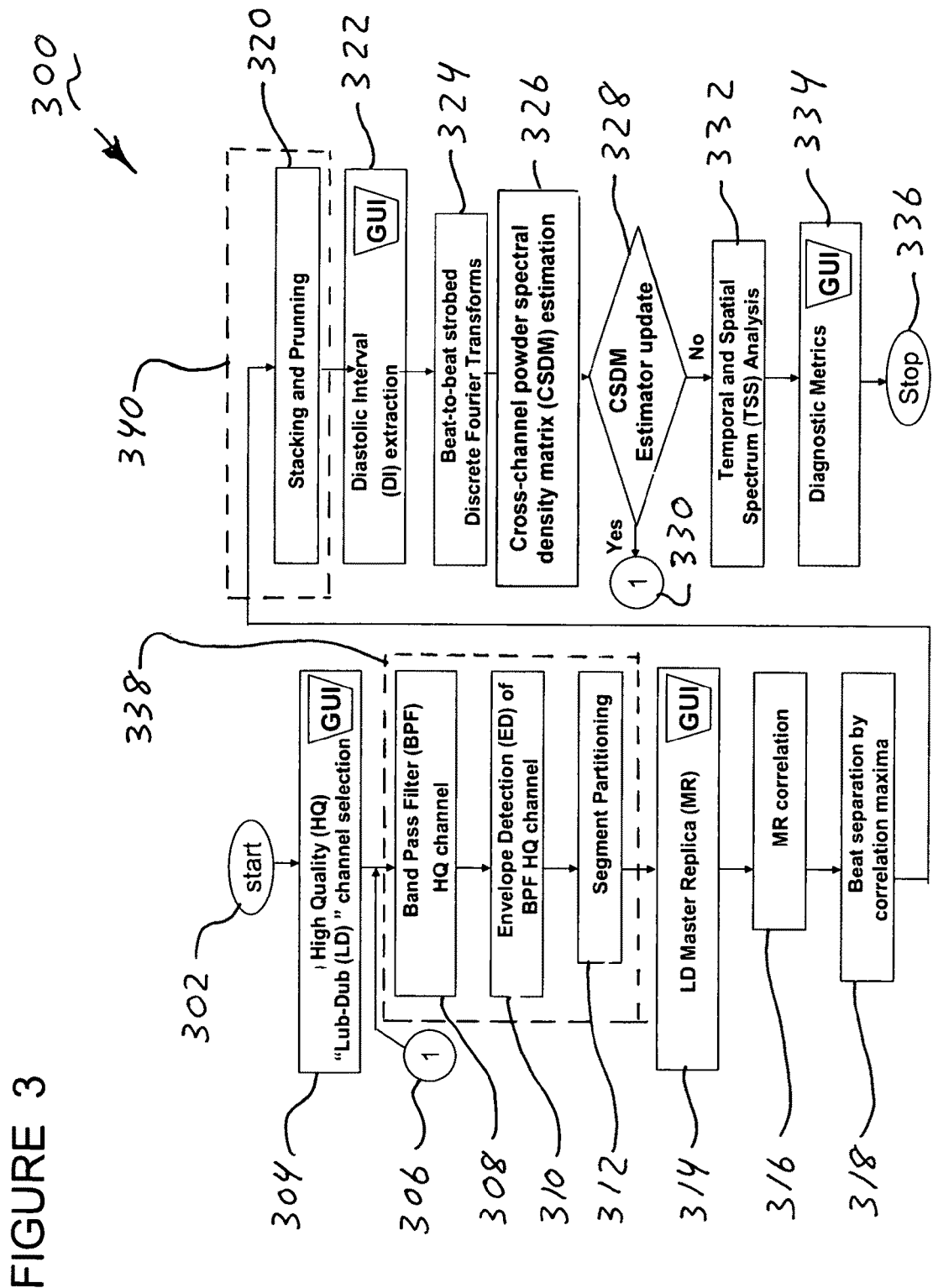
FIG. 3 illustrates a method for processing vibrational cardiac data, according to embodiments of the invention.

FIG. 3 illustrates, generally at 300, a method for processing vibrational cardiac data, according to embodiments of the invention. The method is applied to vibrational cardiac data that is measured with an array of N sensing transducers, which are mounted on the surface of a human's body as described above in conjunction with the previous figures. With reference to FIG. 3, a method starts at a block 302.

Figure 4:
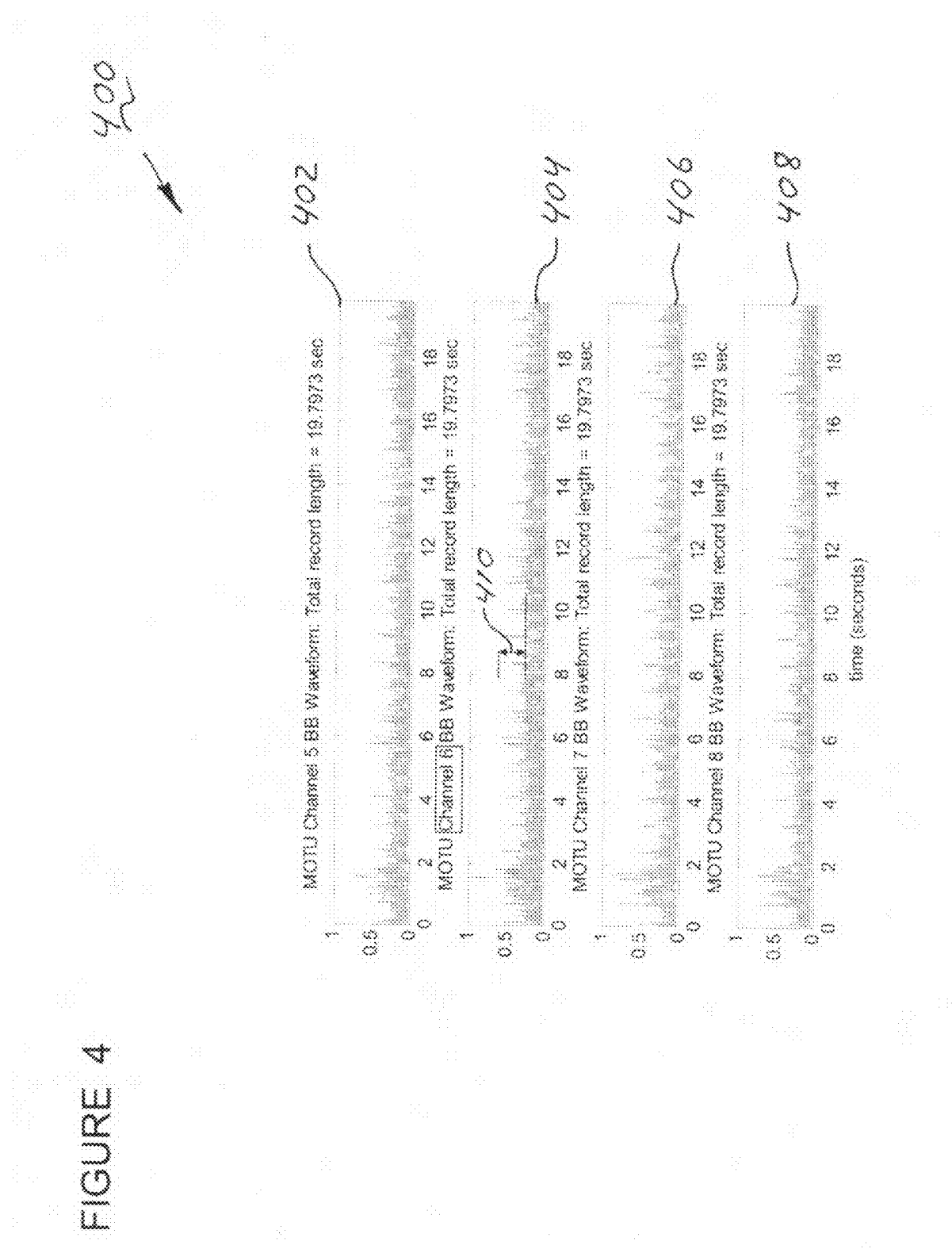
FIG. 4 illustrates several channels of vibrational cardiac data, according to an embodiment of the invention.

For the purpose of extracting diastolic intervals from their respective heart cycles, at a block 304 a technician selects a single high quality channel from the array of N sensing transducers. A high quality channel has a high signal-to-noise ratio, wherein the signal-to-noise ratio is expressed as the ratio between the height of a first peak of a heart cycle and the background level during the diastolic interval and the height of a second peak of the heart cycle and background level of the vibrational cardiac data. The selection of a high quality channel can be performed by a technician or it can be automated in a selection algorithm that would be performed by a data processing system such as the computer system (data acquisition system) described above in conjunction with FIG. 1B. FIG. 4 illustrates, generally at 400, several channels 402, 404, 406, and 408 of vibrational cardiac data according to an embodiment of the invention. In this example, Channel 6 indicated at 404 is selected as the high quality channel, with signal-to-noise ratio metric indicated at 410.

Optionally, at a block 308, the vibrational cardiac data from the high quality channel is band pass filtered to suppress energy at frequencies that are above and below the frequency content of the first and second peaks of the heart cycle. The band pass filter operation typically passes energy in the band from approximately 5 cycles per second (Hz) to several tens of Hz.

Optionally, at a block 310, envelope detection can be applied to the vibrational cardiac data from the high quality channel. Envelope detection operation is given by:

$$e(t)=abs(x(t)).$$

and can be performed before the band-pass filter operation of block 310. $x(t)$ is the high quality channel vibrational cardiac data time series, abs is the absolute value operator, and $e(t)$ is the envelope amplitude.

Optionally, one or more segments of heart cycle data can be collected to provide the entire heart waveform as described above. When multiple segments are collected, a master replica is selected from each segment.

With reference to FIG. 3, at a block 314, a master replica is selected from the high quality channel, which was specified at the block 304. The master replica is selected by selecting a heart cycle that is highly representative of a majority of heart cycles within the segment of the heart waveform represented by the high quality channel. The master replica is either a portion of or the entire heart cycle so identified. To illustrate the process, FIG. 4 displays vibrational cardiac data, generally at 400, collected from four (4) different transducer channels, i.e., a channel five (5) at 402, a channel six (6) at 404, a channel seven (7) at 406 and a channel eight (8) at 408. The vibrational cardiac data collected from channel six (6) at 404 (FIG. 4) will be used for master replica selection and correlation due to favorable signal-to-noise characteristics as indicated at 410.

Figure 5:
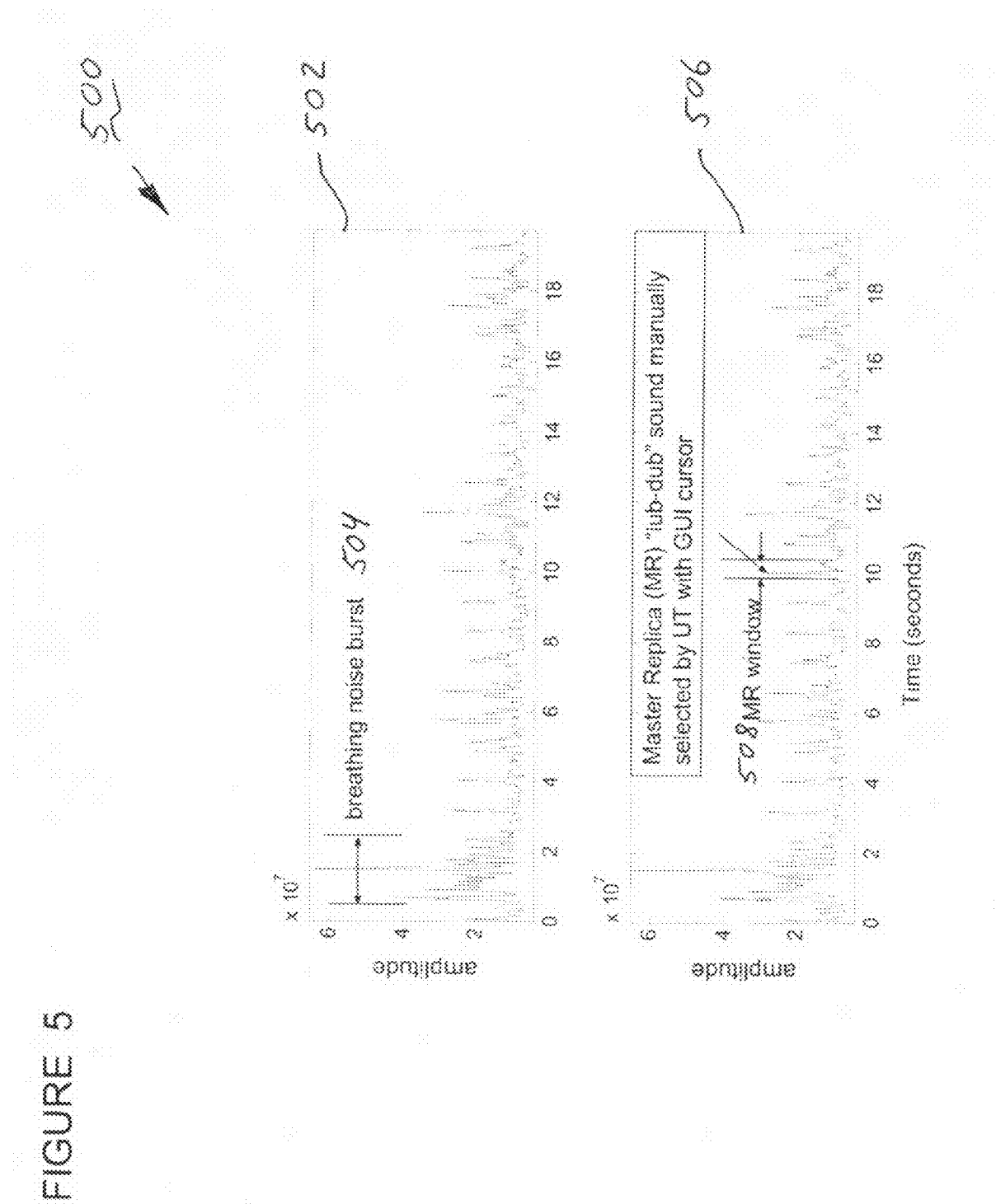
FIG. 5 illustrates master replica selection according to an embodiment of the invention.

Optionally, the data from 404 can be band-pass filtered, as described at the block 306 (FIG. 3) and is displayed as 502 in FIG. 5. FIG. 5 illustrates, generally at 500, master replica selection according to an embodiment of the invention. A noise burst due to breathing is marked at 504 and the same band-pass filtered data is displayed again at 506 where the master replica (MR) window is indicated at 508.

At a block 316 the master replica is correlated with the high quality channel vibrational cardiac data from which it was selected. This cross-correlation procedure produces a correlation waveform that is a function of the time lag between the master replica and the segment waveform extending over the entire length of the segment minus the time length of the master replica. The correlation waveform has local maxima when the master replica is temporally well aligned as a function of time lag with a corresponding high signal-to-noise ratio portion of the segment waveform. These local maxima establish time reference points that are used to identify the diastolic window and to align successive heart cycles in time, i.e., synchronize, for signal analysis.

Figure 6:
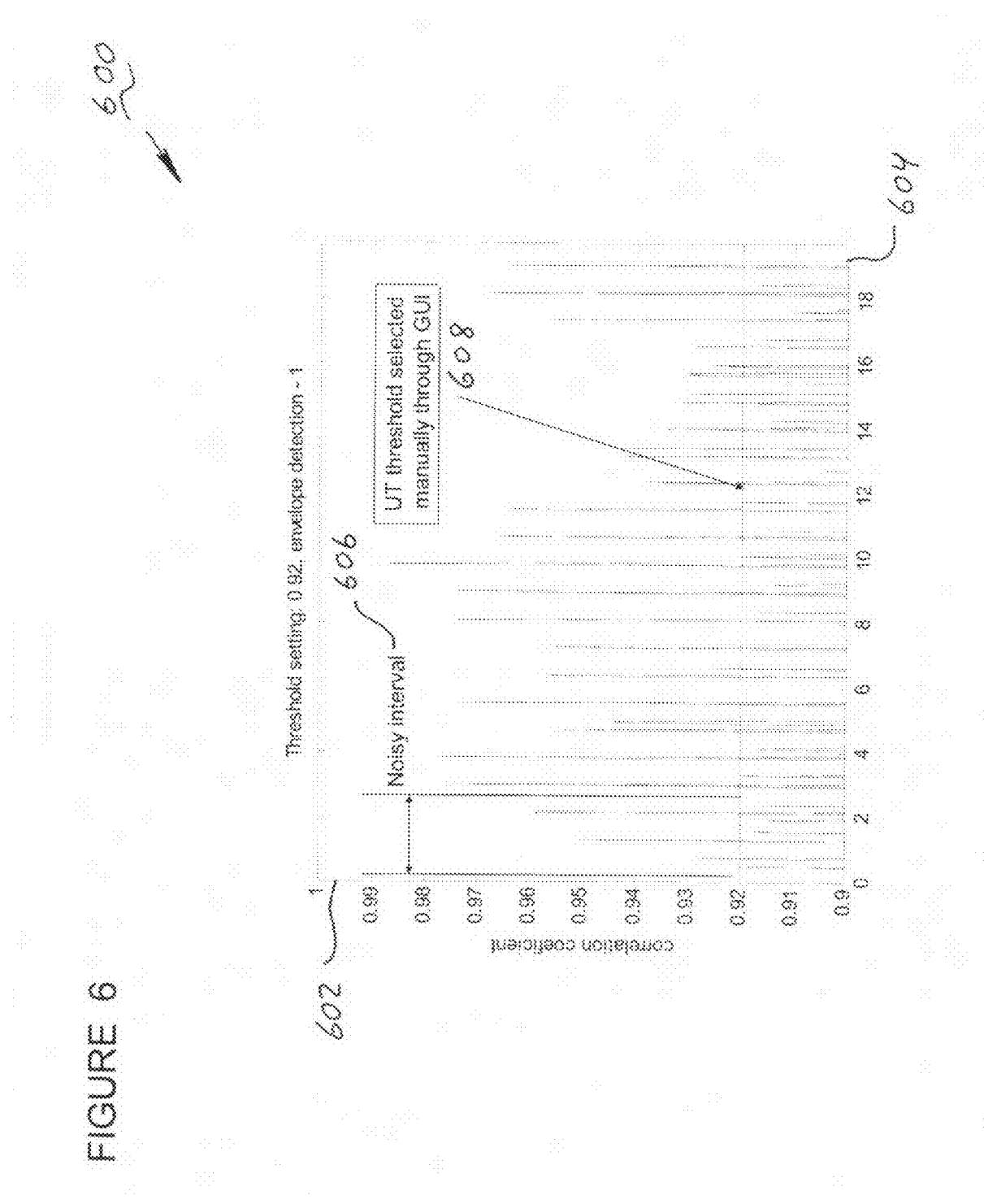
FIG. 6 illustrates, in one embodiment, a correlation scan.

At a block 318, the local maxima identified in the block 316 are used to separate heart cycles from a segment as a function of time. FIG. 6 illustrates, in one embodiment, a correlation scan, generally at 600, that resulted from the vibrational cardiac data shown at 506 in FIG. 5. With reference to FIG. 6, in one embodiment, the process begins by analyzing the correlation data 602 to locate local maxima for all values of time (t) for which the correlation coefficient c(t) is:

$$c(t) > \max[c(t-1)\ c(t+1)].$$

Next, all values for which c(t) falls below a threshold are discarded. With reference to FIG. 6, correlation coefficient c(t) is plotted at 602 as a function of time 604. A threshold is indicated at 608. The threshold 608 can be defined by an operator with a graphical user interface (GUI) or it can be defined by the system.

Next, a time difference is obtained between a correlation peak and the peak that came before it in time. If the time difference is less than a threshold, then the maximum peak value is discarded as a possible heart beat cycle starting time. This process discards all candidate heart cycle starting times for heart cycles with a heart rate greater than a specified threshold. For example, a 0.5 second time difference threshold would disallow heart rates above 120 beats per minute (bpm). The local maxima that are left are used to identify the heart cycles from which the vibrational cardiac data will be extracted and processed. Generally lower values of correlation coefficient can be observed in interval 606 which correspond with the effects of breathing noise.

Figure 7:
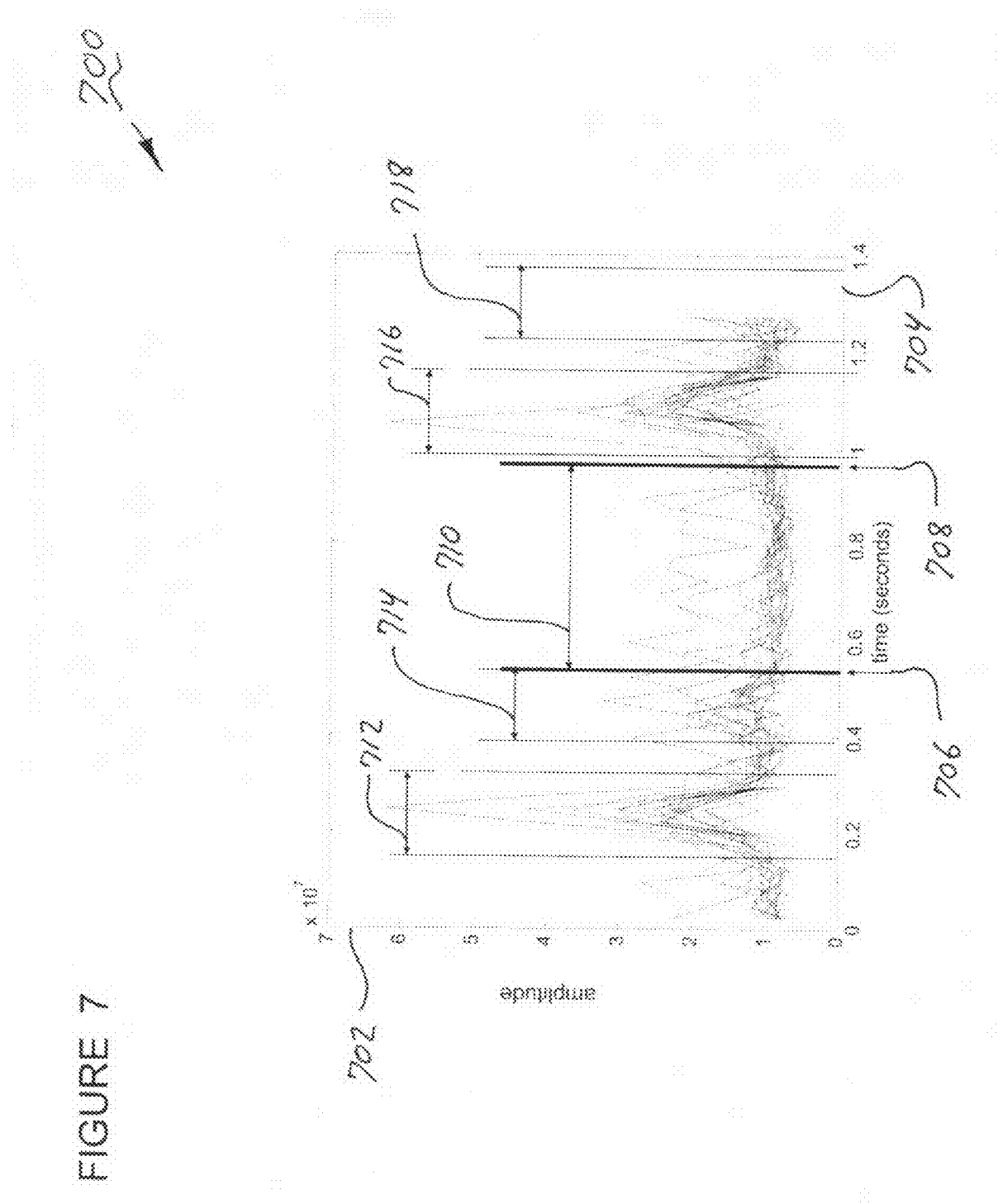
FIG. 7 illustrates, in one embodiment, assembling multiple heart cycles.

Corresponding with a block 320 (FIG. 3), FIG. 7 illustrates, in one embodiment, assembling multiple heart cycles. With reference to FIG. 7, the local maxima that are identified by the analysis described above in conjunction with the block 318 are used to define windows in time as the window starting times. The vibrational cardiac data corresponding to these windows in time are over plotted as illustrated, where amplitude is indicated on an axis 702 and time along an axis 704. Envelope amplitude maxima 712 and 714 are followed by a diastolic interval 710. Envelope amplitude maxima 716 and 718 are used to help the identification of the diastolic interval; however it is not mandatory to use all four Envelope amplitude maxima to locate the diastolic interval 710. A single envelope amplitude maxima and knowledge of the human's heart beat rate are sufficient to identify the diastolic interval 710. A start time 706 and a stop time 708 are placed at the ends of the diastolic interval either by a technician or these indicators can be located automatically by an algorithm in an automated process.

Optionally, for each of the diastolic intervals indicated at 710, a power parameter, such as average squared amplitude over the duration of the heart cycle is computed for each heart cycle. Then all of the average squared amplitude levels are averaged to produce a mean squared amplitude level averaged over all heart cycles over plotted. Each heart cycle's average squared amplitude level is compared to a multiple of the mean squared level and is discarded if its value exceeds the multiple of the mean squared level. In one embodiment the multiple is equal to 2.0. This heart cycle waveform pruning operation is used to discard those heart cycles that are contaminated by noise which is likely due to breathing and/or intestinal activity.

Figure 8:
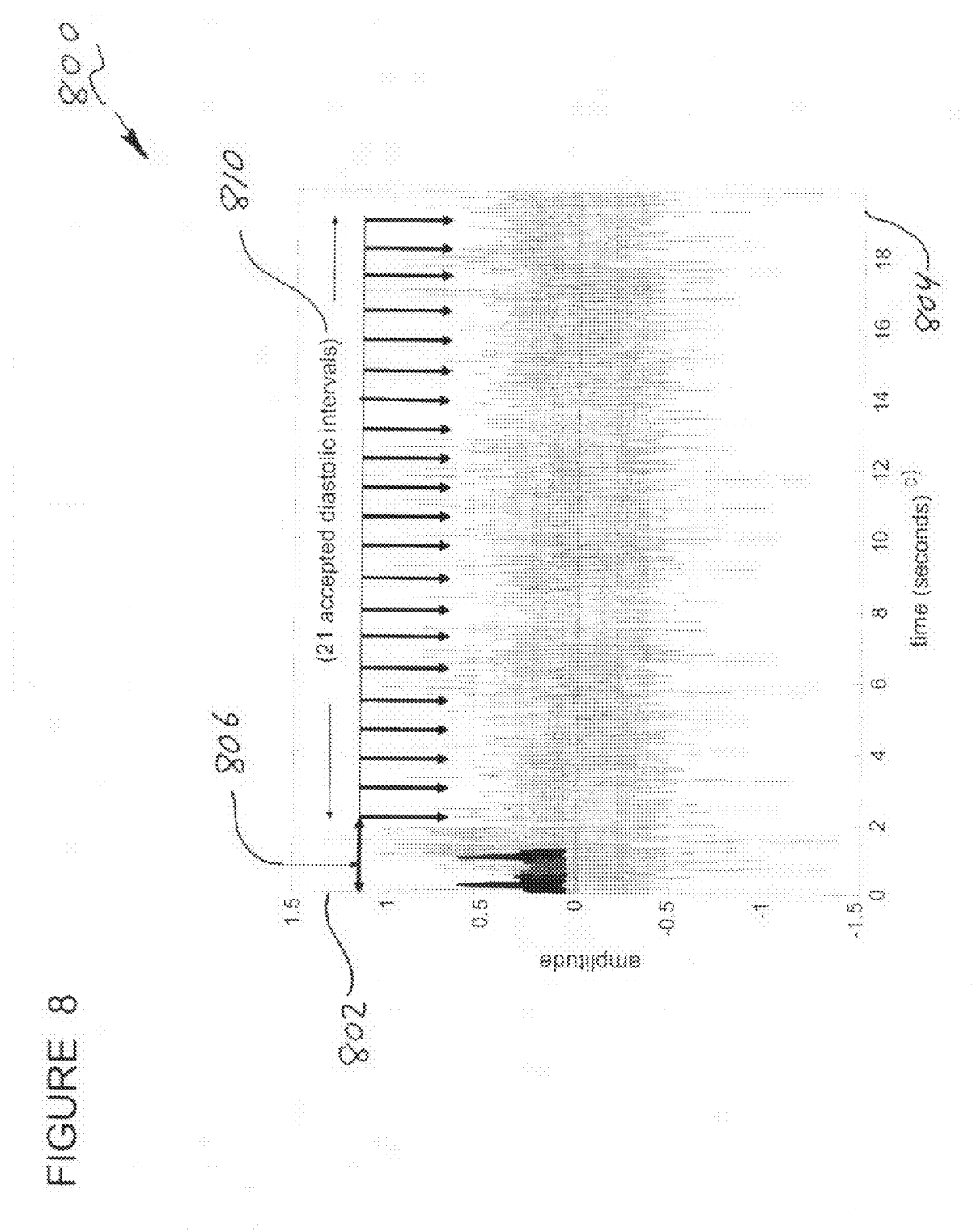
FIG. 8 illustrates, in one embodiment, diastolic intervals selected for further processing.

Corresponding with a block 322 (FIG. 3), FIG. 8 illustrates, in one embodiment; generally at 800, diastolic intervals selected for further processing. With reference to FIG. 8, using the heart cycle starting times, estimated above in conjunction with the previous figures, e.g., FIG. 7, a subsequence of adjacent time samples are extracted from the vibrational cardiac data 810. In FIG. 8, vibrational cardiac data from a high quality transducer channel are plotted with amplitude on an axis 802 and time on an axis 804. Vibrational cardiac data are accepted from 21 diastolic intervals. The intervals marked at 806 are contaminated with excessive noise and are rejected.

Corresponding with a block 324 (FIG. 3), the vibrational cardiac data that are extracted during the identical time window for all N sensors channels, from the diastolic windows, can be processed as a continuous ensemble of data or the diastolic window can be further partitioned into subintervals or slots as described above. Referring back to FIG. 2, the diastolic window 212 is divided into four 4 slots 214 and the next diastolic window 232 is partitioned into four (4) slots 234. Adjacent time slots with the slots 214 or 234 can overlap in time. The slots have fixed starting times relative to the respective diastolic interval and are typically separated by less than one tenth of an average heart cycle (for example, 0.1 seconds for a 60 beat per minute heart cycle). In one embodiment, the length of the slot interval, in number of time samples, is taken to be the number of points in a discrete Fast Fourier Transform (FFT) operation which is performed independently within each slot. This procedure effectively strobes the same time slot number (e.g. 1, 2, 3, 4, etc.) from each heart cycle for FFT spectrum analysis. In various embodiments, the temporal length of an FFT window slot is in the range of 0.15±0.1 seconds. Thus, for each sensor channel, a complex Fourier spectrum of the vibrational cardiac data is computed from the time series data.

Figure 9:
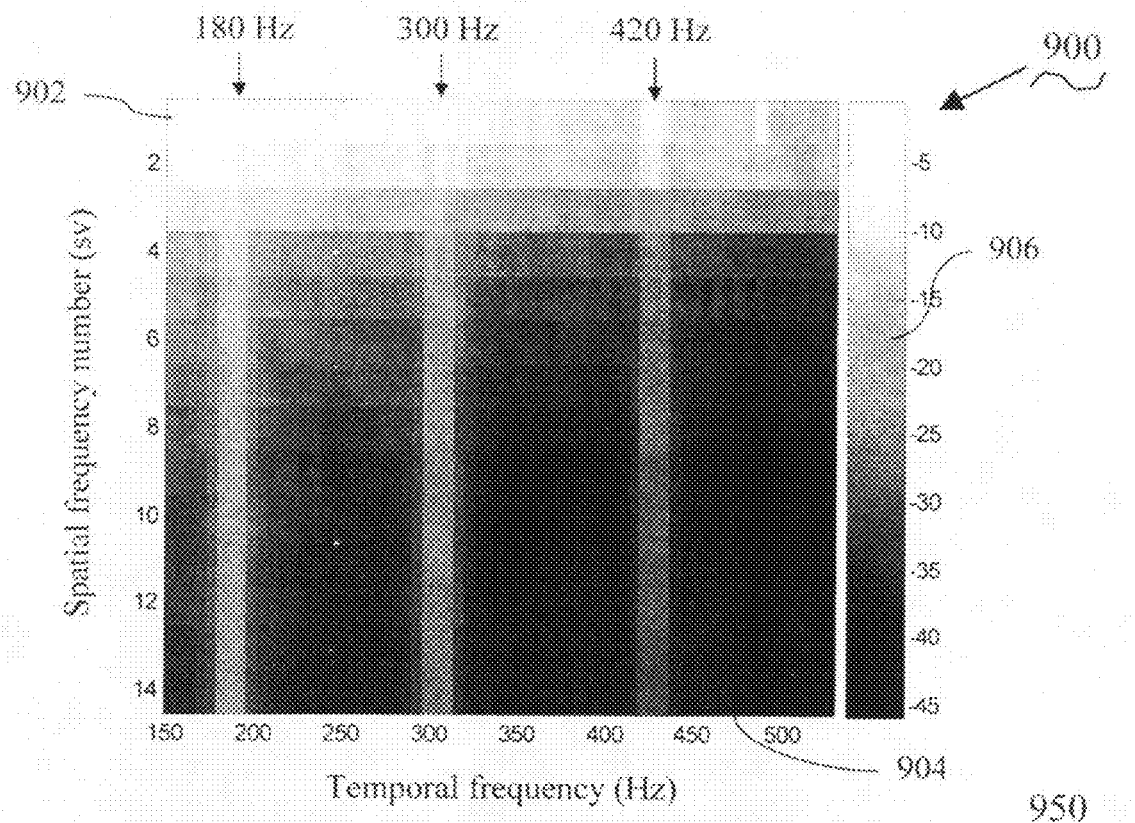
FIG. 9 illustrates a two-dimensional space-time frequency power spectrum (orthogonal vibration mode decomposition of the cross-channel power spectral density matrix "CSDM") of vibrational cardiac data, according to one embodiment of the invention.
Figure 9:
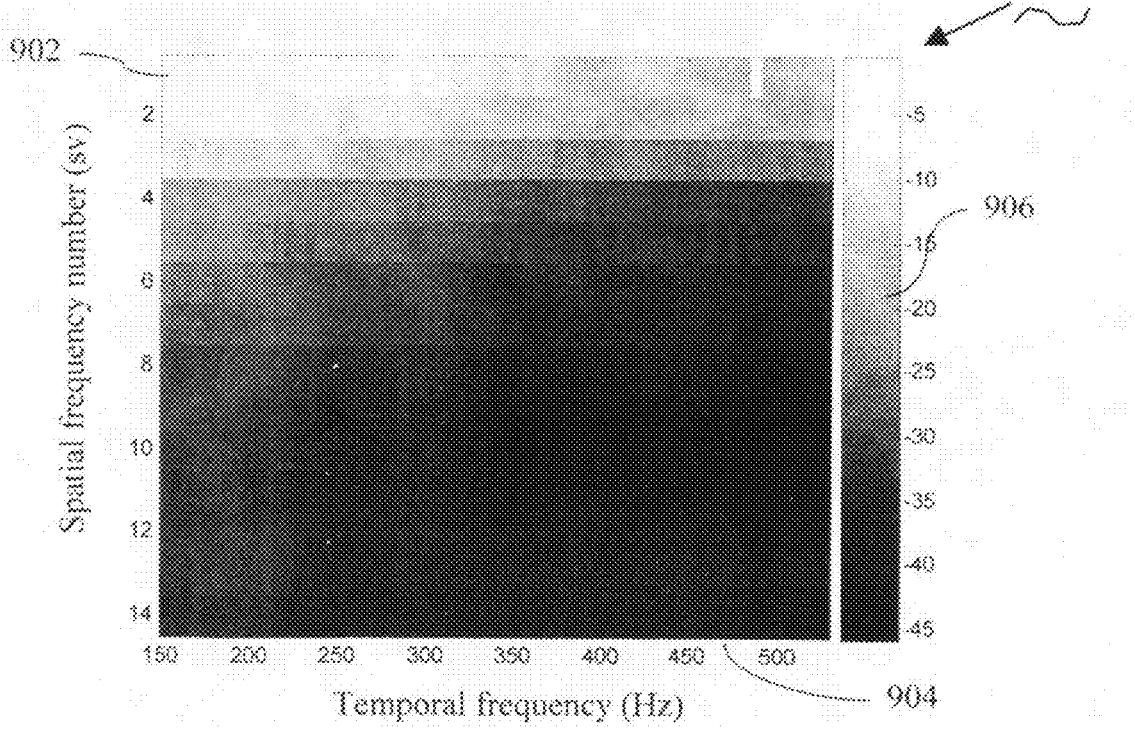

Corresponding with a block 326 (FIG. 3), FIG. 9 illustrates a two-dimensional space-time frequency power spectrum (cross-channel power spectral density matrix "CSDM" of vibrational cardiac data, generally at 900, according to one embodiment of the invention. With reference to FIG. 9, spatial frequency number is plotted on an axis 902 and temporal frequency is plotted on an axis 904. Normalized amplitude is indicated by a grey scale color and a reference key is illustrated at 906.

The CSDM is either computed for the entire heart cycle, based on averaging all heart cycles in the entire heart waveform or it can optionally be computed for the a specific slot number in the heart cycle. In either case, the CSDM is computed by placing the complex Fourier spectrum (FFT outputs), obtained by processing the transducer channel outputs, into a four-dimensional matrix indexed as x(n, b, k, m):

$$x(b, k, m) = \begin{bmatrix} x(1, b, k, m) \\ x(2, b, k, m) \\ \vdots \\ x(N, b, k, m) \end{bmatrix}$$

where n is the vibration transducer number, k is the FFT discrete frequency bin number, b is the retained heart beat count, and m is the slot number. In cases where a heart waveform contains multiple segments, heart beat count b will span multiple time segments, where each segment corresponds to a breath holding period as described above.

With N as the number of vibration transducer channels, the CSDM is then an N-by-N complex Hermitian R(k, m) matrix. R(k, m) is calculated as a time average over the heart beat count index b, separately for each frequency bin k, and slot number m, according to:

$$R(k, m) = \frac{1}{B}\sum_{b=1}^{B} x(b, k, m)^* x(b, k, m)'$$

Where B is the number of heart beat cycles in the averaging ensemble which can span multiple segments of acquired vibrational transducer data in some embodiments. The value of B will depend on the number of separate transducer channels processed for a given measurement. Generally, a lower bound for the value of B is approximately four (4) times the number of transducers, N. A preferred value for B is eight (8) to ten (10) times N. Those of skill in the art will recognize that the goal in selecting the value for B is to reduce the variance in the estimation of the CSDM matrix, therefore the value of B can be set at various numbers and the values of eight (8) to ten (10) are illustrative and not limiting.

Corresponding with a block 328 (FIG. 3), the processes from a block 306 to the block 326 are repeated as needed for each segment in the heart waveform. Thus, if the heart waveform contains more than one segment, control transfers from 330 to the block 306 and the intervening process blocks are repeated. Note, that for each segment in the heart waveform, a new master replica is chosen and a correlation step is performed on a segment-by-segment basis. This process accommodates variations in heart rate within a segment and the time averaging in the CSDM process (block (326)) spans the time epoch for all segments acquired and processed within a heart waveform.

Figure 10:
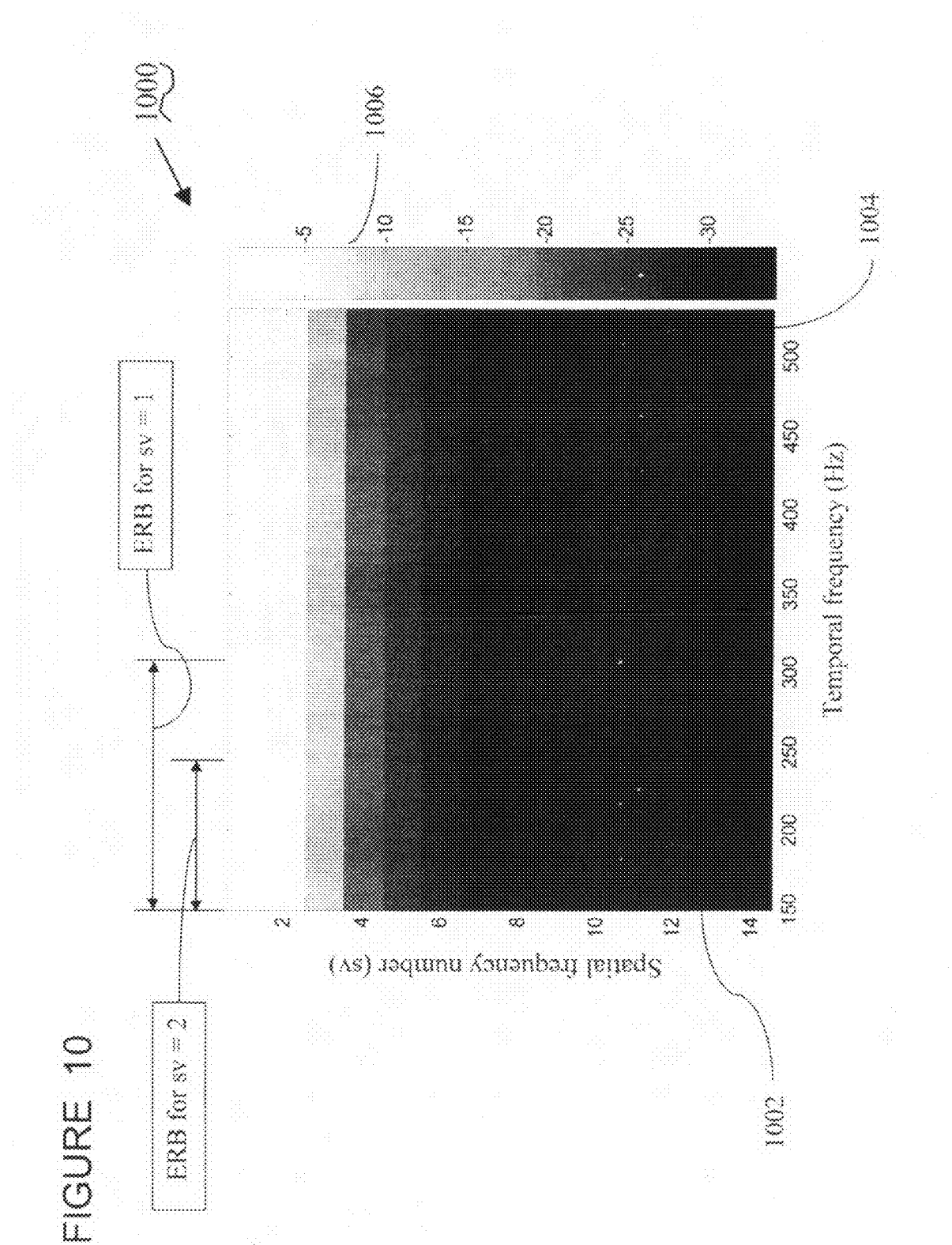
FIG. 10 illustrates a two-dimensional space-time frequency power spectrum processed for Equivalent Rectangular Bandwidth, according to one embodiment of the invention.

Corresponding with a block 332 (FIG. 3), FIG. 10 illustrates a two-dimensional space-time frequency power spectrum (Temporal-Spatial Spectrum (TSS)) processed for Equivalent Rectangular Bandwidth (ERB), generally at 1000, according to one embodiment of the invention. With reference to FIG. 10, temporal frequency is plotted on an axis 1004 and eigenvalue number/index (Spatial frequency number (sv)) is plotted on an axis 1002. Relative amplitude 1006 of the data is displayed as a modulation of gray scale. Following completion of the CSDM calculation (block (330)), an eigenvalue-eigenvector decomposition (EED) of the CSDM in each slot and for each FFT frequency bin in the range $k_{low} \leq k \leq k_{high}$ is computed. This decomposition of the CSDM provides estimates of the blood flow turbulence induced noise spectrum level and bandwidth.

With N transducer channels, the distribution of energy in the CSDM eigenvalues at each frequency also quantifies the degree of angular concentration of spatial radiation points. The metric of spatial distribution of energy sources is referred to herein as spatial bandwidth and is non-parametric since it does not require a propagation model parameterization, including wave speed, of the non-homogeneous body medium 112 (FIG. 1A) through which the wave energy propagates from the turbulent induced noise location within the artery (FIG. 1A).

The EED is calculated according to:

[M(k, m), L(k, m), M(k, m)]=svd(R(k, m))

where M(k, m) is the N-by-N matrix of orthonormal eigenvectors of (R(k, m)) as columns and L(k, m) is the diagonal matrix of corresponding eigenvalues arranged in monotonically decreasing order from the upper left to lower right.

In one embodiment, to establish a noise floor for the analysis, the smallest $N_f$ eigenvalues are averaged over all FFT frequency values and then these frequency averages are in turn, averaged over the smallest $N_f$ values. This produces a two dimensional space-time average. The number $N_f$ is typically ten to thirty percent of the total number of transducer channels, N, and the frequency bins over which frequency averaging is performed are within the range above 100. This two dimensional averaged eigenvalue, $\lambda_0$, is termed the TSS noise floor. The TSS noise floor sets a threshold, over which an accumulation (summation) of eigenvalues is performed. This accumulation of eigenvalues contains an estimate of the blood flow turbulence induced noise energy.

For the largest p=1, 2, 3, ..., $N-N_f$ eigenvalues, all of the eigenvalues as a function of frequency for a fixed value of p that exceed a threshold given by $\alpha\lambda_0$ are counted by integer counter $C_{s(p)}$ and averaged as $\lambda_{s(p)}$ and those that do not exceed the threshold are counted by $C_{n(p)}$ also averaged as $\lambda_{n(p)}$.

Referring back to FIG. 9, the CSDM eigenvalues are plotted along the vertical axis as a function of frequency (horizontal axis) for the sample case described herein. The estimation of the CSDM presented in FIG. 9 has been obtained by time averaging the "slot 1" interval processed data over five segments with a total of ninety (90) heart cycles. The $3^{rd}$, $5^{th}$, and $7^{th}$ harmonics of the 60 cycle power line artifact are evident in the data. Subsequently, these artifacts are nulled, blocked, and extrapolated through, which effectively notches out the FFT frequency bins as illustrated in the image at 950. Similar processing can be performed on the other slots within the diastolic interval.

Corresponding with a block 334 (FIG. 3), referring back to FIG. 10, The counter $C_{s(p)}$ when multiplied by the FFT frequency bin width (equal to the numerical inverse of the FFT interval in seconds) is termed the Equivalent Rectangular spectral Bandwidth, ERB, for spatial eigenvalue p. The estimated number set $C=[C_{s(p)}, \lambda_{s(p)}, C_{n(p)}, \lambda_{n(p)}, \alpha, \lambda_0$ for p=1, 2, ..., $N-N_f]$ can provide a diagnostic tool for the detection of arterial blood flow turbulence and thereby the causative pathology. A simulation of such detection was performed on a phantom and is described below in conjunction with FIG. 11 through FIG. 14.

Referring back to FIG. 10, presentation of the set C in relative terms, shows that the magnitudes of the temporal frequency bandwidth counter $C_{s(p)}$ and the Signal-to-Noise Ratio (SNR) metric $(\lambda_{s(p)}/\lambda_0)$ are in proportion to and therefore a positively correlated marker for blood flow turbulence. In addition, the extent to which the threshold is crossed for larger values of p is in proportion to the extent of spatial distribution, i.e. spatial bandwidth, of the arterial occlusions that result in blood flow turbulence.

In other embodiments, different algorithms can be used to express Equivalent Rectangular Bandwidth (ERB). All such expressions maintain both long-time averaged and spatial-temporal spectrum analysis of the signals from an array of vibration sensors. In one such alternative embodiment, the temporal eigenvalue spectrum for each spatial frequency index, L(k, p), $k_{low} \leq k \leq k_{high}$, for each spatial frequency index, p, is searched over the temporal frequency index k for the point at which the level has decreased to a pre-specified value (e.g. −3 db, −6 db, ...) relative to the maximum value. This embodiment is appropriate where the shape of the eigenvalue spectrum has a monotonically decreasing trend with increasing k.

The process begins by pre-smoothing the estimated frequency spectrum as a least squares fit of log10(L(k, p)) to a two parameter linear function over the range of k. Such smoothing permits a specific value of $k=C_{s(p)}$ at the specified reduced value threshold point relative to the maximum value, $\log 10(L(k_{low},p))$, to be identified. Given the estimated value of $k=C_{s(p)}$ at the specified reduced value level threshold, for each of p=1, 2, . . . , N, the eigenvalues as a function of frequency, k, that exceed the threshold are given by the averaged value above the threshold as $\lambda_{s(p)}$ and those that do not exceed the threshold are counted by $C_{n(p)}$ and expressed by the averaged value below the threshold as $\lambda_{n(p)}$.

In this alternative embodiment, the estimated number set $C'=[C_{s(p)}, \lambda_{s(p)}, C_{n(p)}, \lambda_{n(p)},$ for p=1, 2, . . . , N] or its functional equivalent, can be used with appropriate human data to provide a diagnostic tool for the detection of arterial blood flow turbulence and the causative pathology. An example of such use is illustrated below in conjunction with FIG. 11 through FIG. 14.

Examination of the set C', shows that the magnitudes of the temporal frequency bandwidth counter $C_{s(p)}$ and the Signal-to-Noise Ratio (SNR) metric ($\lambda_{s(p)}/\lambda_{n(p)}$,) are in proportion to and are therefore a positively correlated marker for the presence of blood flow turbulence. This alternative embodiment can be generalized by performing higher order approximations to the estimated eigenvalue spectrum and thereby increasing the number of parameters subjected to a diagnostic process. On this issue, the example presented above embodies the lowest possible complexity.

Figure 11:
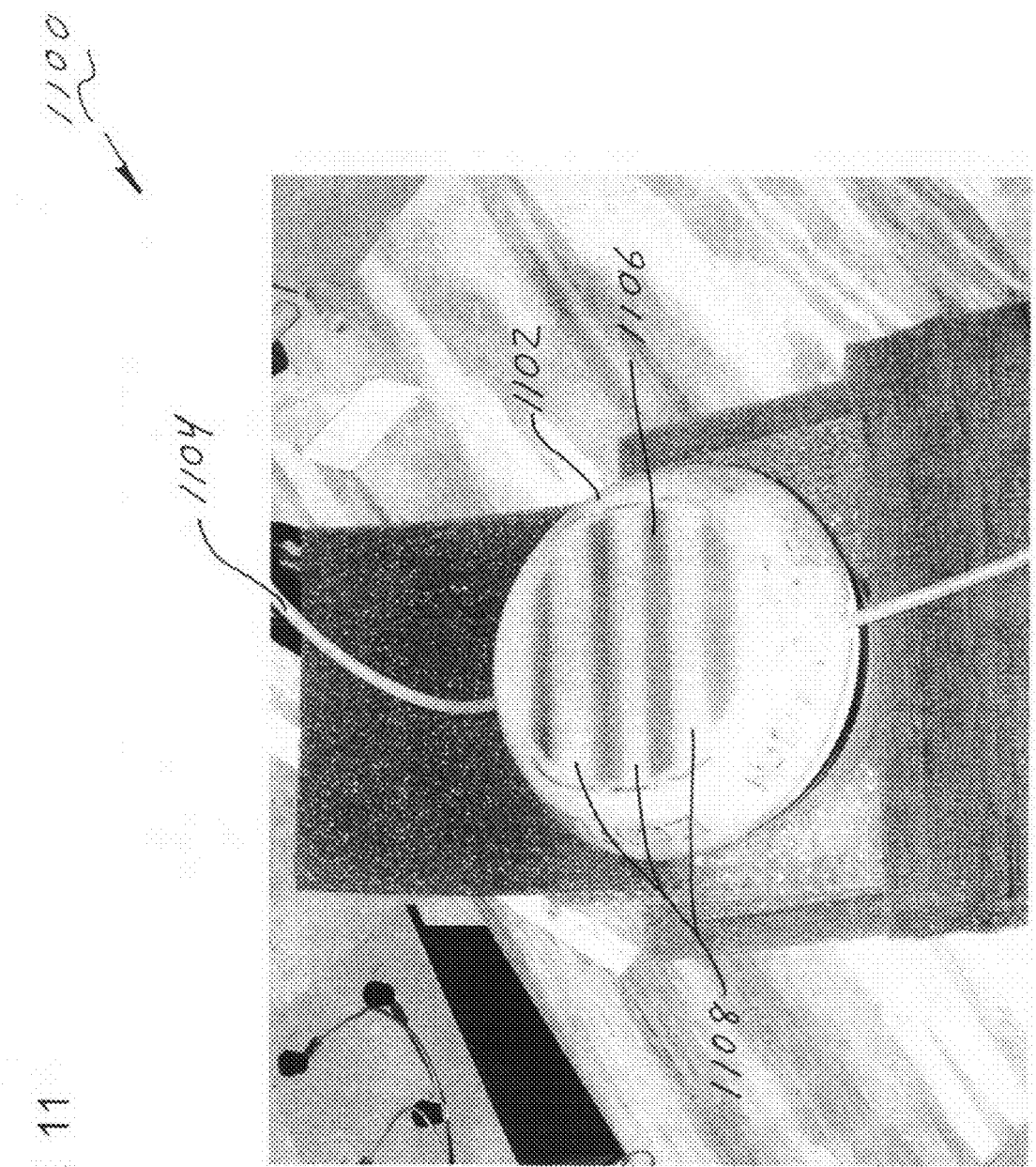
FIG. 11 illustrates a phantom constructed to simulate blood flow through an area of stenosis, according to one embodiment of the invention.

FIG. 11 illustrates a phantom, generally at 1100, constructed to simulate blood flow through an area of stenosis, according to one embodiment of the invention. With reference to FIG. 11, a phantom simulator of the human thorax 1102 in the vicinity of the chest wall was formed from silicone gel 1106 with a predetermined stiffness comparable to human tissue. The phantom contained high-stiffness human rib surrogates 1108 made of shaped plastic. Blood flow was simulated within a latex tube 1104 having cross-sectional characteristics typical of the left anterior descending (LAD) human coronary artery with a 3.0 millimeters (mm) inner diameter. Fluid flow occluders of different topologies were inserted into the latex tubing and the blood was simulated in viscosity with mixtures of 25 to 50% glycol and distilled water. All dimensions were known and the latex tube was embedded at a depth of 40 mm from the contiguous surface of the phantom.

The long axis of the vibration sensor linear array (not shown) was placed parallel to the rib surrogates 1108 and directly over the linear space between a pair of the rib surrogates 1108. Such placement simulates placement on a human and established a direct vibration wave path from the induced turbulent flow site to the vibration sensors located on the contiguous surface of the phantom.

Figure 12:
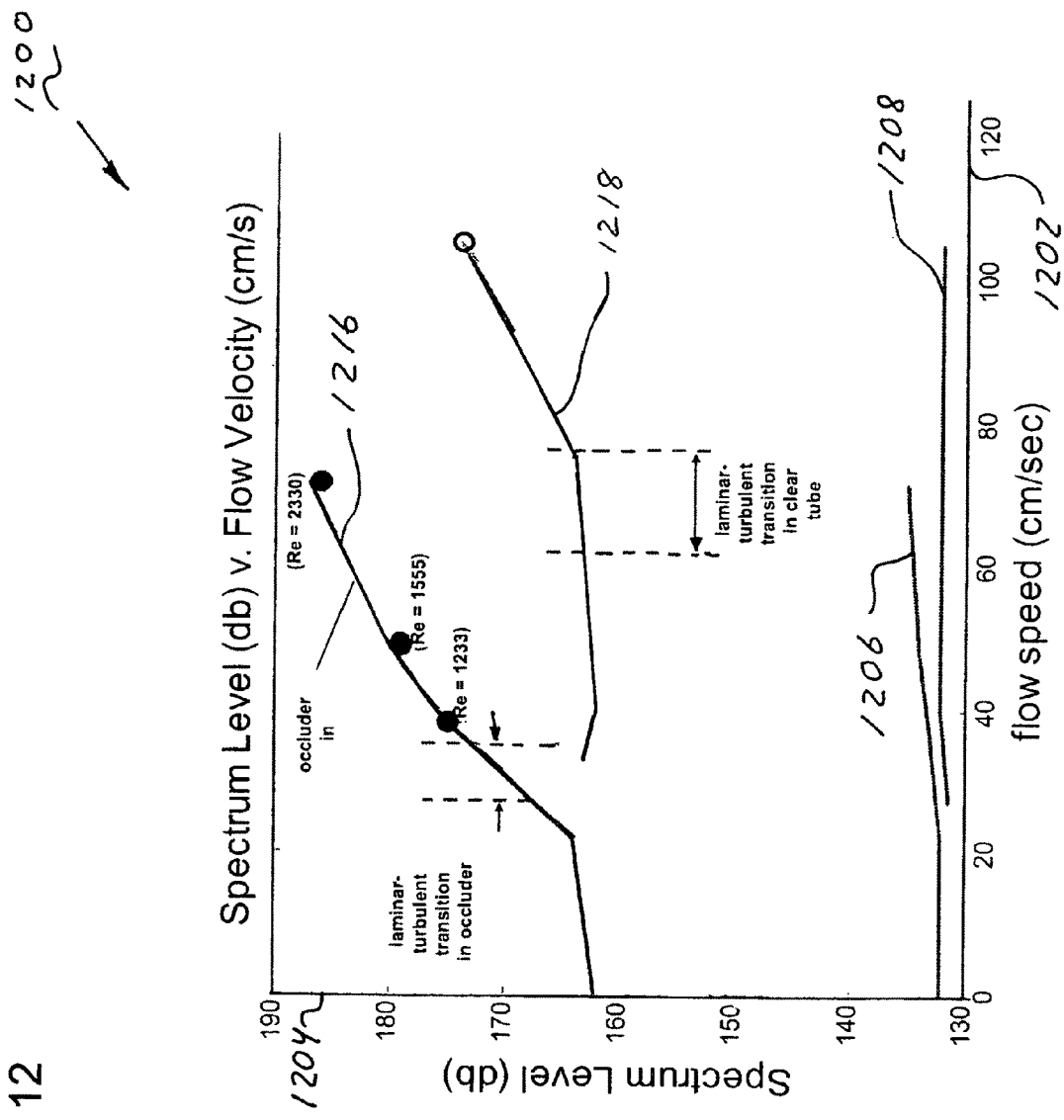
FIG. 12 illustrates detection of stenosis in a phantom, according to embodiments of the invention.

FIG. 12 illustrates detection of stenosis occlusion in a phantom, generally at 1200, according to embodiments of the invention. With reference to FIG. 12, the measured power spectrum level of vibration transducers is plotted on a vertical axis 1204. Spectrum level represents an integration in frequency of the energy in a given eigenvalue. Flow speed is plotted on an axis 1202. A series of experiments were conducted with different flow speeds with and without an occluder present in the latex tube 1104 (FIG. 11) to simulate an area of stenosis in a human.

One experiment consisted of comparing the case of a high flow rate, 72 cm/sec, without occluder (to induce turbulence) to a realistic human diastolic LAD flow rate, 35 cm/sec, with occluder induced flow turbulence (to simulate stenosis in a human). The higher flow rate had more than four times the laminar flow kinetic energy than the lower flow rate wherein turbulence was induced by the occluder. The objective of this experiment was to quantify the vibrational energy levels from both flow regimes and to evaluate the sensitivity of the methods described herein as a procedure for discriminating phantom simulated pathological flow from normal unoccluded flow (healthy no stenosis) at a very high level in order to produce a worst case detection scenario.

FIG. 12 shows the Measured Power Spectrum level (relative decibels, db) versus fluid flow rate (cm/sec) for flow "with occluder" at 1216 and "without occluder" at 1218. Plotted in FIG. 12 are the maximum and minimum eigenvalues, sv01 and sv14, respectively, of the 14 sensor array estimated Cross-Spectral Density matrix (CSDM). Eigenvalue sv14 is shown at 1206 with occluder and at 1208 without occluder. Eigenvalue sv01 is plotted at 1216, as a function of flow speed, with occluder in to simulate an area of stenosis. Eigenvalue sv01 is plotted at 1218 without occluder to simulate the healthy state, free of stenosis.

FIG. 12 illustrates that the vibrational energy detected at the surface of the phantom is larger in all cases, with the occluder present and low flow rate, than even the very high 100 cm/sec flow rate with no occluder present. Of particular interest for detecting stenosis in humans is the condition of occluded flow (1216) for velocities above 40 cm/sec, the detected levels remain above that for unoccluded flow (1218) even at a flow velocity of 100 cm/sec. Such results demonstrate a capability for discrimination between even very high flow rates without occluder induced noise (1218) and nominally low flow rates with occluder produced turbulence (1216).

Figure 13:
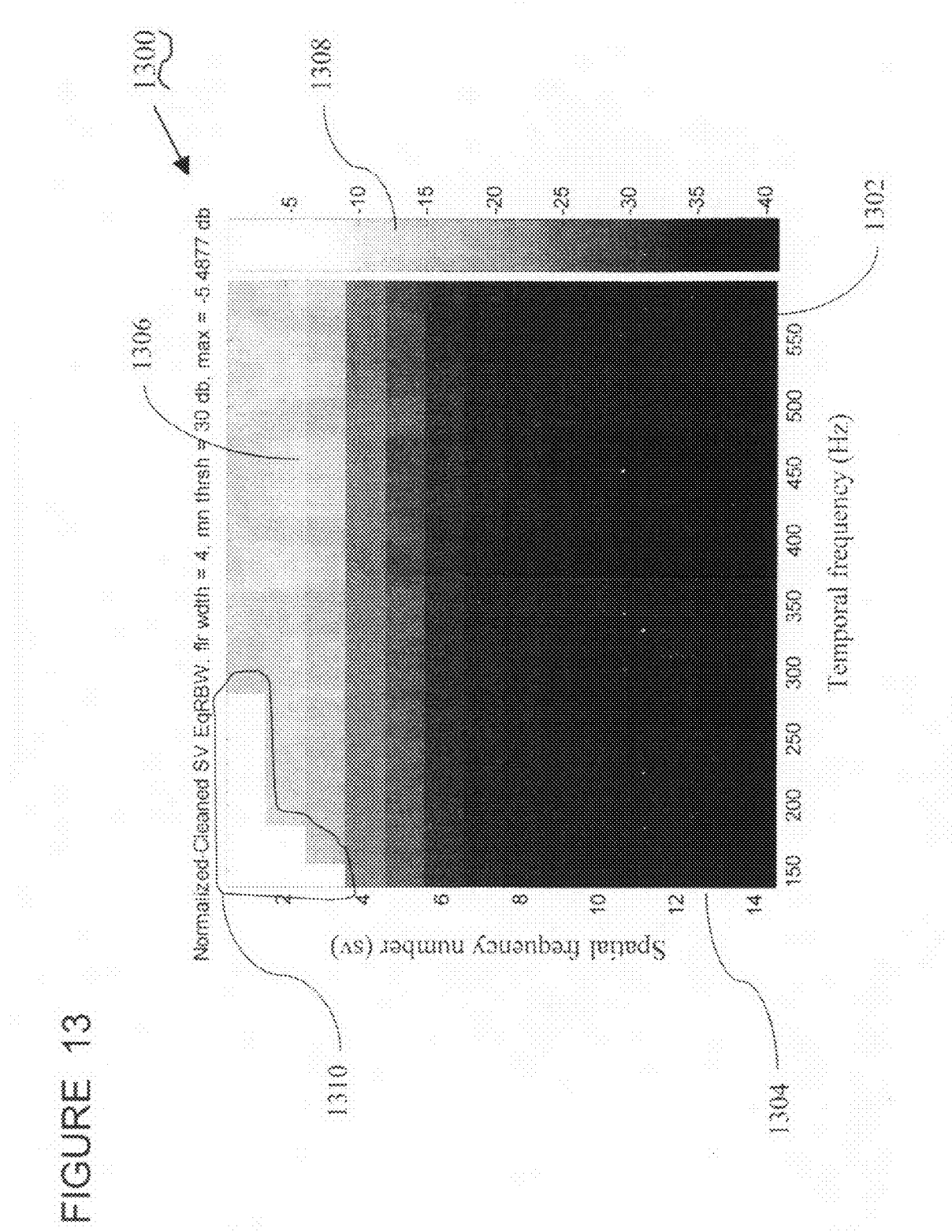
FIG. 13 illustrates an Equivalent Rectangular bandwidth (ERB) display of vibrational energy resulting from fluid flow with occluder present in a phantom (area of stenosis), according to one embodiment of the invention.

FIG. 13 illustrates an Equivalent Rectangular bandwidth (ERB) display of vibrational energy resulting from fluid flow with occluder present (area of stenosis), generally at 1300, according to one embodiment of the invention. With reference to FIG. 13, temporal frequency is plotted on an axis 1302 and eigenvalue number/index is plotted on an axis 1304. Relative amplitude 1308 of the data 1306 is displayed as a modulation of gray scale. Data 1306 represents an Equivalent Rectangular Bandwidth (ERB) estimate for the 35 cm/sec flow rate with an occluder present.

Figure 14:
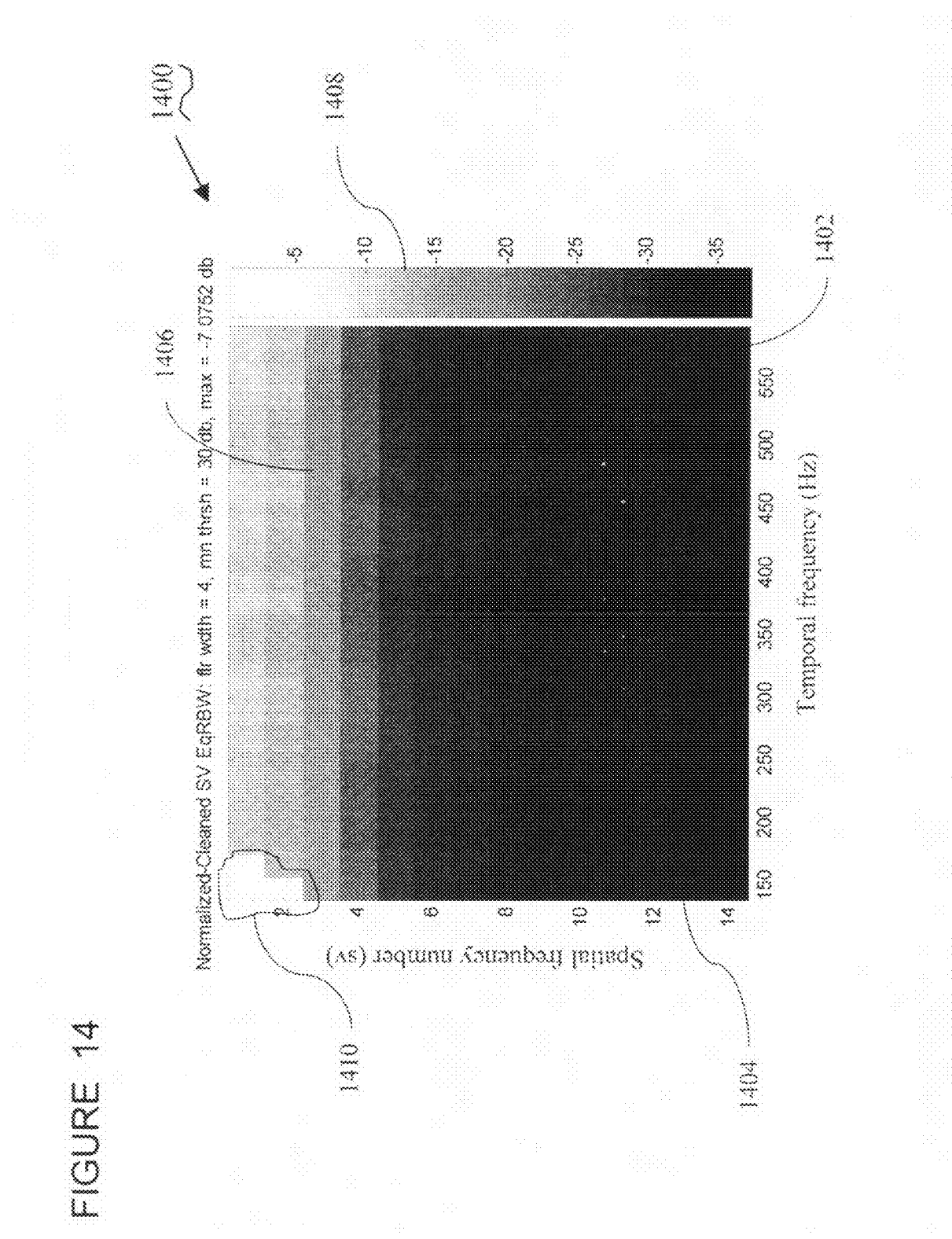
FIG. 14 illustrates an Equivalent Rectangular bandwidth (ERB) estimate of vibrational energy resulting from fluid flow without occluder in a phantom (healthy condition without stenosis), according to one embodiment of the invention.

FIG. 14 illustrates an Equivalent Rectangular bandwidth (ERB) estimate of vibrational energy resulting from fluid flow without occluder (healthy condition without stenosis), generally at 1400, according to one embodiment of the invention. With reference to FIG. 14, the same format is used to present the data from the 14 channel array, temporal frequency is plotted on an axis 1402 and eigenvalue number/index is plotted on an axis 1404. Relative amplitude 1408 of the data 1406 is displayed as a modulation of gray scale. The flow rate of the simulated blood flow was 72 cm/sec. Such a rate is higher than what typically exists during normal blood flow in a healthy human. This high rate (72 cm/sec) was selected for purposes of comparison in order to present a worst case detection scenario for the methods described herein.

FIG. 13 shows that three spatial frequency eigenvalue modes 1310 are excited with sufficient energy to exceed the 3 db ERB threshold for the 35 cm/sec flow velocity. In contrast, FIG. 14 indicates that only two spatial modes 1410 exceed the ERB threshold level at a notably small value of the estimated ERB. The discrimination provided by these two extreme cases illustrates the presence of detected turbulent flow induced noise.

For purposes of discussing and understanding the embodiments of the invention, it is to be understood that various terms are used by those knowledgeable in the art to describe techniques and approaches. Furthermore, in the description, for purposes of explanation, numerous specific details are set forth in order to provide a thorough understanding of the present invention. It will be evident, however, to one of ordinary skill in the art that the present invention may be practiced without these specific details. In some instances, well-known structures and devices are shown in block diagram form, rather than in detail, in order to avoid obscuring the present invention. These embodiments are described in sufficient detail to enable those of ordinary skill in the art to practice the invention, and it is to be understood that other embodiments may be utilized and that logical, mechanical, electrical, and other changes may be made without departing from the scope of the present invention.

Some portions of the description may be presented in terms of algorithms and symbolic representations of operations on, for example, data bits within a computer memory. These algorithmic descriptions and representations are the means used by those of ordinary skill in the data processing arts to most effectively convey the substance of their work to others of ordinary skill in the art. An algorithm is here, and generally, conceived to be a self-consistent sequence of acts leading to a desired result. The acts are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, waveforms or the like.

It should be borne in mind, however, that all of these and similar terms are to be associated with the appropriate physical quantities and are merely convenient labels applied to these quantities. Unless specifically stated otherwise as apparent from the discussion, it is appreciated that throughout the description, discussions utilizing terms such as "processing" or "computing" or "calculating" or "determining" or "displaying" or the like, can refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

An apparatus for performing the operations herein can implement the present invention. This apparatus may be specially constructed for the required purposes, or it may comprise a general-purpose computer, selectively activated or reconfigured by a computer program stored in the computer. Such a computer program may be stored in a computer readable storage medium, such as, but not limited to, any type of disk including floppy disks, hard disks, optical disks, compact disk read-only memories (CD-ROMs), and magnetic-optical disks, read-only memories (ROMs), random access memories (RAMs), electrically programmable read-only memories (EPROM)s, electrically erasable programmable read-only memories (EEPROMs), FLASH memories, magnetic or optical cards, etc., or any type of media suitable for storing electronic instructions either local to the computer or remote to the computer.

The algorithms and displays presented herein are not inherently related to any particular computer or other apparatus. Various general-purpose systems may be used with programs in accordance with the teachings herein, or it may prove convenient to construct more specialized apparatus to perform the required method. For example, any of the methods according to the present invention can be implemented in hard-wired circuitry, by programming a general-purpose processor, or by any combination of hardware and software. One of ordinary skill in the art will immediately appreciate that the invention can be practiced with computer system configurations other than those described, including hand-held devices, multiprocessor systems, microprocessor-based or programmable consumer electronics, digital signal processing (DSP) devices, network PCs, minicomputers, mainframe computers, and the like. The invention can also be practiced in distributed computing environments where tasks are performed by remote processing devices that are linked through a communications network.

The methods of the invention may be implemented using computer software. If written in a programming language conforming to a recognized standard, sequences of instructions designed to implement the methods can be compiled for execution on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, application, driver, . . . ), as taking an action or causing a result. Such expressions are merely a shorthand way of saying that execution of the software by a computer causes the processor of the computer to perform an action or produce a result.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing code on a computer, the expression of that technique may be more aptly and succinctly conveyed and communicated as a formula, algorithm, or mathematical expression. Thus, one of ordinary skill in the art would recognize a block denoting A+B=C as an additive function whose implementation in hardware and/or software would take two inputs (A and B) and produce a summation output (C). Thus, the use of formula, algorithm, or mathematical expression as descriptions is to be understood as having a physical embodiment in at least hardware and/or software (such as a computer system in which the techniques of the present invention may be practiced as well as implemented as an embodiment).

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc.

As used in this description, "one embodiment" or "an embodiment" or similar phrases means that the feature(s) being described are included in at least one embodiment of the invention. References to "one embodiment" in this description do not necessarily refer to the same embodiment; however, neither are such embodiments mutually exclusive. Nor does "one embodiment" imply that there is but a single embodiment of the invention. For example, a feature, structure, act, etc. described in "one embodiment" may also be included in other embodiments. Thus, the invention may include a variety of combinations and/or integrations of the embodiments described herein.

While the invention has been described in terms of several embodiments, those of skill in the art will recognize that the invention is not limited to the embodiments described, but can be practiced with modification and alteration within the spirit and scope of the appended claims. The description is thus to be regarded as illustrative instead of limiting.

What is claimed is:

1. A method of obtaining cardiac data comprising:
    acquiring vibrational cardiac data from a transducer wherein the transducer measures vibration of a surface of a human's body;
    selecting a master replica from a segment of the vibrational cardiac data;
    cross-correlating the master replica with the segment to obtain a plurality of local maxima; and
    extracting vibrational cardiac data that were emitted during a diastolic interval from each heart cycle with the aid of the plurality of local maxima.

2. The method of claim 1, further comprising:
    filtering the segment before the selecting, wherein the filtering performs a band-pass filter operation on the segment.

3. The method of claim 2, further comprising:
    performing an envelope detection on the segment before the filtering.

4. The method of claim 1, further comprising:
    computing an average amplitude for the vibrational cardiac data obtained during the extracting; and
    discarding vibrational cardiac data that deviates by more than a specified amount from the average amplitude.

5. The method of claim 1, wherein the master replica is a portion of the segment.

6. The method of claim 5, wherein the portion is selected from the group consisting of a fraction of a heart cycle, one heart cycle, and more than one heart cycle.

7. The method of claim 1, further comprising:
    picking a high quality transducer channel from an array of N transducer channels, wherein the vibrational cardiac data is collected from the high quality transducer channel.

8. The method of claim 7, wherein a number of heart cycles collected is approximately equal to ten to fifteen times N.

9. The method of claim 1, wherein the selecting is performed by a human operator.

10. The method of claim 1, wherein vibrational cardiac data contains a plurality of segments.

11. The method of claim 10, wherein the plurality is equal to six segments.

12. The method of claim 10, wherein the human starts the acquiring to coincide with breath-hold and stops the acquiring to coincide with non-breath hold.

13. The method of claim 1, wherein the segment includes a continuous period of time during which the human can comfortably refrain from breathing.

14. The method of claim 1, wherein the segment contains approximately 120 heart cycles.

15. The method of claim 1, wherein the segment contains Approximately 20 heart cycles.

16. The method of claim 1, wherein the extracting further comprises:
    discarding a local maxima whose amplitude is below an amplitude threshold value.

17. The method of claim 16, wherein the extracting further comprises:
    comparing a separation in time between adjacent local maxima against a time threshold value and discarding the latter local maxima when the separation is below the time threshold value.

18. The method of claim 1, wherein the extracting is assisted by a human operator and the human operator sets a start time and optionally an end time for the diastolic interval.

19. The method of claim 1, further comprising:
    computing a mean power level for all vibrational cardiac data collected during diastolic intervals in a segment;
    comparing an average power level for vibrational cardiac data collected during a diastolic interval to the mean power level and discarding the vibrational cardiac data if the average power level deviates from the mean power level by a predetermined amount.

20. The method of claim 1, wherein a peak of a correlation coefficient is normalized to a value of one.

21. The method of claim 1, further comprising:
    evaluating the vibrational cardiac data obtained from the extracting for a condition of blood flow turbulence.

22. The method of claim 21, wherein the condition of blood flow turbulence is evaluated further for a condition of stenosis in an artery.

23. The method of claim 21, wherein the evaluating compares the vibrational cardiac data to a reference spectrum level and the reference spectrum level is related to vibrational cardiac data obtained when stenosis is substantially not present.

24. The method of claim 21, wherein the evaluating compares the vibrational cardiac data to a reference spectrum level and the reference spectrum level is related to vibrational cardiac data obtained when stenosis is present.

25. The method of claim 21, wherein the evaluating compares the vibrational cardiac data to a reference spectrum level and the reference spectrum level is obtained from the vibrational cardiac data.

26. A method for processing acquired synchronized diastolic interval vibrational cardiac data (DI data) collected by an array of transducers during a plurality of heart cycles from a human, comprising:
    performing a time-to-frequency transformation on the DI data, wherein the performing is applied to the DI data acquired from each transducer during the plurality of heart cycles to obtain a plurality of transducer channel frequency complex Fourier spectra;
    calculating a cross-channel spectral density matrix (CSDM) from the plurality of transducer frequency spectra, wherein the CSDM is calculated as a time average over the time synchronized plurality of heart cycles;
    performing an eigenvalue-eigenvector decomposition (EED) of the CSDM to obtain a spatial frequency number versus temporal frequency representation of the DI data.

27. The method of claim 26, further comprising:
    partitioning a diastolic interval into S time slots, wherein the performing the time-to-frequency transformation is done separately within each slot number of the S time slots.

28. The method of claim 27, wherein S is selected from the group consisting of 1, 2, 3, 4, 5, and 6.

29. The method of claim 28, wherein the duration of a time slot is approximately one-third the duration of a diastolic interval and adjacent time slots may overlap in time.

30. The method of claim 26, wherein the time-to-frequency transformation is a Fast Fourier Transform (FFT) operation.

31. The method of claim 28, wherein a time-to-frequency transformation is performed for the slot number within each heart cycle of the plurality of time synchronized heart cycles, to produce a plurality of time-to-frequency transformations, then the plurality of time-to-frequency transformations are averaged across the plurality of heart cycles for the slot number.

32. The method of claim 26, wherein the time average extends over more than one segment.

33. The method of claim 32, wherein a new master replica has been selected from each segment in order to obtain the DI data.

34. The method of claim 27, wherein the time-to-frequency transformation is a discrete Fast Fourier Transform (DFFT) operation and the CSDM (R(k, m)) is calculated as a time average over a heart beat count index b, and separately for each frequency bin "k" and slot number "m," with N equal to the number of vibration transducer channels, according to:

$$R(k, m) = \frac{1}{B}\sum_{b=1}^{B} x(b, k, m)^* x(b, k, m)'$$

where $$x(b, k, m) = \begin{bmatrix} x(1, b, k, m) \\ x(2, b, k, m) \\ \vdots \\ x(N, b, k, m) \end{bmatrix}$$

35. The method of claim 34, wherein the EED of the DI data is calculated as:
[M(k, m), L(k, m), M(k, m)]=svd(R(k, m)); where
M(k, m) is the N-by-N matrix of orthonormal eigenvectors of R(k, m) as columns and L(k, m) is the diagonal matrix of corresponding eigenvalues in monotonic decreasing order and "svd" indicates "Singular Value Decomposition."

36. The method of claim 35, further comprising:
computing a two dimensional Temporal and Spatial Spectrum (TSS) noise floor $\lambda_0$ of the DI data, wherein DI data for a subset $N_f$ of eigenvalues of R(k,m) are averaged over all FFT frequency values to produce a subset of frequency averages, then the subset of frequency averages are averaged over the subset $N_f$ of eigenvalues, thereby producing the two dimensional Temporal and Spatial Spectrum (TSS) noise floor $\lambda_0$ of the DI data.

37. The method of claim 36, wherein a size of the subset $N_f$ of eigenvalues is between 10 and 30 percent of N.

38. The method of claim 36, further comprising:
performing a summation $\lambda_{s(p)}$, over frequency, of eigenvalues as a function of frequency, for a fixed value of p, on the DI data, for the $C_{s(p)}$ eigenvalues of the DI data that exceed a threshold given by $\alpha\lambda_0$,; and the summation proceeds from p=1, 2, . . . , N−$N_f$, and
performing a summation $\lambda_{n(p)}$, over frequency, of eigenvalues as a function of frequency, for a fixed value of p, on the DI data, for the eigenvalues of the DI data that do not exceed the threshold given by $\alpha\lambda_0$.

39. The method of claim 26, further comprising:
correcting the DI data for artifacts of 60 cycle/sec and harmonic, room ambient electromagnetic interference before the calculating by nulling and extrapolating the frequency spectrum through a 60 cycle artifact in at least one of the plurality of transducer frequency complex Fourier spectra.

40. The method of claim 38 further comprising:
computing an Equivalent Rectangular Bandwidth (ERB) of the DI data for the p-th spatial eigenvalue, wherein the ERB=$C_{s(p)}$*(FFT frequency resolution), and $C_{s(p)}$ is a counter used during the summation $\lambda_{s(p)}$.

41. The method of claim 35, further comprising:
presmoothing a frequency spectrum of the EED; and
calculating an Equivalent Rectangular Bandwidth (ERB) of the DI data by identifying the frequency at which the LLS fit decreases to a specified level with increasing frequency.

42. An apparatus comprising:
a data processing device configured to accept acquired diastolic interval vibrational cardiac data (DI data) collected by an array of transducers during a plurality of heart cycles;
a computer readable medium containing executable computer program instructions, which when executed by the data processing system, cause the data processing system to perform a method comprising:
partitioning a diastolic interval into S time slots;
performing a time-to-frequency transformation on the DI data acquired within a slot of the S time slots, wherein the performing is applied to the DI data acquired from each transducer to obtain a plurality of transducer complex frequency spectra;
calculating a cross-channel spectral density matrix (CSDM) from the plurality of transducer complex frequency spectra, wherein the CSDM is calculated as a time average over a plurality of heart cycles; and
performing an eigenvalue-eigenvector decomposition (EED) of the CSDM to obtain a spatial frequency number verses temporal frequency representation of the DI data.

43. The apparatus of claim 42, wherein the method further comprises:
computing an Equivalent Rectangular Bandwidth (ERB) of the DI data for the p-th spatial eigenvalue, wherein the ERB=$C_{s(p)}$*(FFT frequency resolution), and $C_{s(p)}$ is a counter used during the summation $\lambda_{s(p)}$.

44. A method for processing cardiac data comprising:
acquiring vibrational cardiac data from an array of transducers wherein the transducers are coupled to a human;
selecting a master replica from a segment of the vibrational cardiac data;
cross-correlating the master replica with the segment to obtain a plurality of local maxima;
extracting vibrational cardiac data that were emitted during a diastolic interval from each heart cycle with the aid of the plurality of local maxima (DI data);
performing a time-to-frequency transformation on the DI data, wherein the performing is applied to the DI data acquired from each transducer during the plurality of heart cycles to obtain a plurality of transducer channel frequency complex Fourier spectra;
calculating a cross-channel spectral density matrix (CSDM) from the plurality of transducer frequency spectra, wherein the CSDM is calculated as a time average over the time synchronized plurality of heart cycles; and
performing an eigenvalue-eigenvector decomposition (EED) of the CSDM to obtain a spatial frequency number versus temporal frequency representation of the DI data.

45. The method of claim 44, further comprising:
partitioning a diastolic interval into S time slots, wherein the performing the time-to-frequency transformation is done separately within each slot number of the S time slots.

46. A method of obtaining cardiac data from a human comprising:
separating an unwanted coronary event from vibrational cardiac data collected from an array of sensors non-invasively from the human's body, wherein the effects of the unwanted coronary event on vibrational cardiac data are reduced by the separating; and
evaluating the vibrational cardiac data, after the separating, for a condition of blood flow turbulence within the human's body.

47. The method of claim 46, wherein the condition of blood flow turbulence is evaluated further for a condition of stenosis in an artery.

48. The method of claim 46, wherein the unwanted event is selected from the group consisting of closure of a heart valve, and blood flow through an open heart valve.

49. The method of claim 46, wherein the vibrational cardiac data were collected during a period of breath-hold.

50. The method of claim 46, wherein the evaluating compares the vibrational cardiac data to a reference spectrum level and the reference spectrum level is related to vibrational cardiac data obtained when stenosis is substantially not present.

51. The method of claim 46, wherein the evaluating compares the vibrational cardiac data to a reference spectrum level and the reference spectrum level is related to vibrational cardiac data obtained when stenosis is present.

52. The method of claim 46, wherein the evaluating compares the vibrational cardiac data to a reference spectrum level and the reference spectrum level is obtained from the vibrational cardiac data.

\* \* \* \* \*